(12) United States Patent
Shepard

(10) Patent No.: US 6,213,040 B1
(45) Date of Patent: Apr. 10, 2001

(54) APPARATUS FOR HIGH-SPEED LACING OF AN ARTICLE

(76) Inventor: Daniel R. Shepard, 186 Atlantic Ave., North Hampton, NH (US) 03862

( * ) Notice: Subject to any disclaimer, the term of this patent is extended or adjusted under 35 U.S.C. 154(b) by 0 days.

(21) Appl. No.: 09/301,241

(22) Filed: Apr. 28, 1999

Related U.S. Application Data

(60) Provisional application No. 60/083,968, filed on May 1, 1998.

(51) Int. Cl.$^7$ ............................. D05B 13/00; D05B 23/00
(52) U.S. Cl. ................................. 112/475.17; 112/470.21
(58) Field of Search ............................. 112/475.17, 10, 112/6, 11, 116, 121, 470.21, 470.22; 289/1.5, 12, 18.1

(56) References Cited

U.S. PATENT DOCUMENTS

| | | | |
|---|---|---|---|
| 356,101 | * | 1/1887 | Dana, Jr. ..................... 112/470.22 X |
| 2,462,178 | | 2/1949 | Ganz . |
| 2,477,053 | * | 7/1949 | Ewer et al. ..................... 112/470.22 |
| 2,883,913 | * | 4/1959 | Piazze ........................ 112/470.21 X |
| 2,993,455 | * | 7/1961 | Baize ............................. 112/470.22 |
| 3,415,209 | | 12/1968 | Ellison et al. . |
| 3,763,799 | * | 10/1973 | Bottcher ..................... 112/470.21 X |
| 3,814,469 | | 6/1974 | Simon . |
| 3,940,169 | | 2/1976 | Kock . |
| 3,957,004 | | 5/1976 | Ketterer et al. . |
| 3,970,022 | | 7/1976 | Kopatz et al. . |
| 4,357,887 | | 11/1982 | Hara et al. . |
| 5,657,712 | | 8/1997 | Romagnoli . |
| 5,797,243 | | 8/1998 | Tagliferri et al. . |

OTHER PUBLICATIONS

Koch, Paul–August, et al., "Grofses Textil–Lexikon", pp. 99–100, Deutsche Verlags–Anstalt Stuttgart, Germany.

* cited by examiner

Primary Examiner—Ismael Izaguirre
(74) Attorney, Agent, or Firm—Kudirka & Jobse, LLP

(57) ABSTRACT

A apparatus for high speed attachment of a cord to a piece of receiving material is characterized by one or more pins which engage the cord, pierce the receiving material and draw the cord through the receiving material from the first side to a second side thereof so that an open loop is formed in the cord on the second side of the receiving material. The pins may be implemented as a push pin and a spreader pin pairs movably mounted relative to each other and each of which are adapted to grasp the cord and penetrate the receiving material. The loop(s) are formed as the push pin and spreader pin move relative to each other. The apparatus further comprises a floating shuttle, not attached to the frame of the apparatus but supported by a series of gear assemblies, which moves relative to the pins and engages an end portion of the cord, drawing the cord through the open loop so as to complete the lacing stitch of the cord through the receiving material. Accordingly, the apparatus operates without any significant reciprocating motion, resulting in a process that can attach a cord to a piece of receiving material at extremely high speeds. The floating shuttle may be applied in any situation where a strand of material such as cord, thread, wire, or fiber is to be attached to a receiving piece of material.

19 Claims, 18 Drawing Sheets

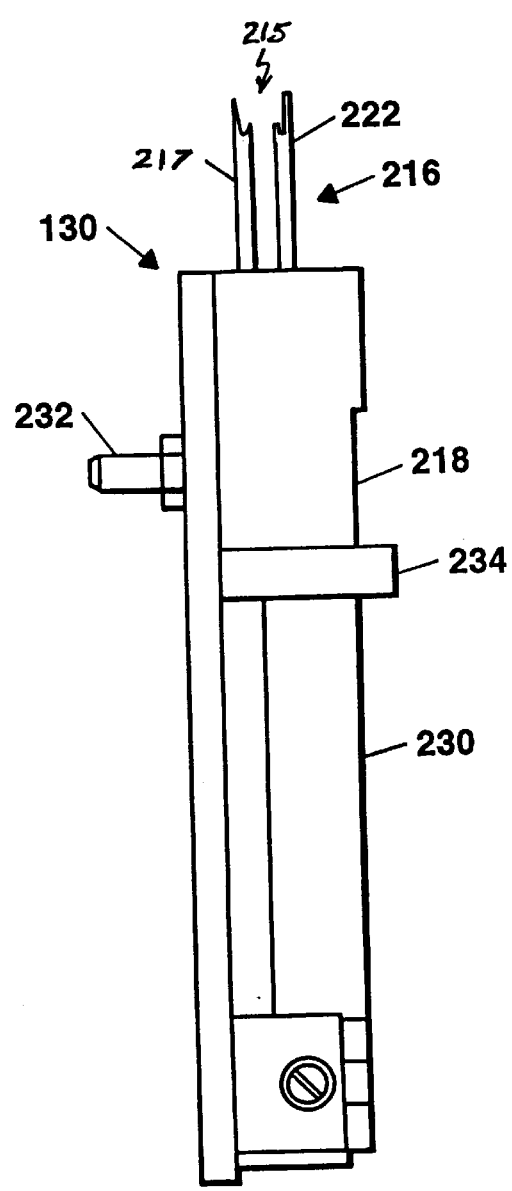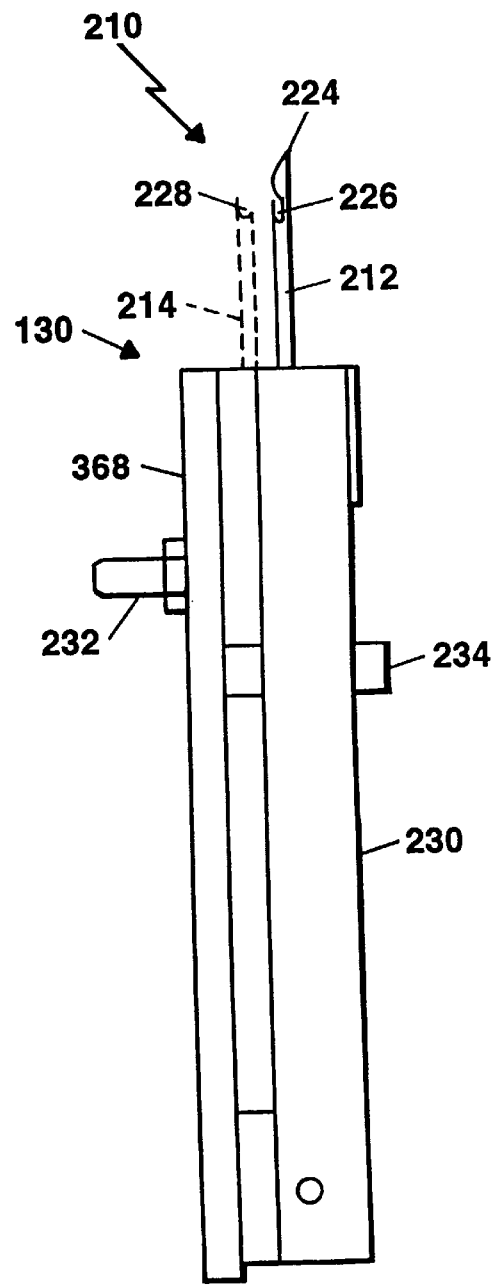
*Figure 2B*          *Figure 2C*

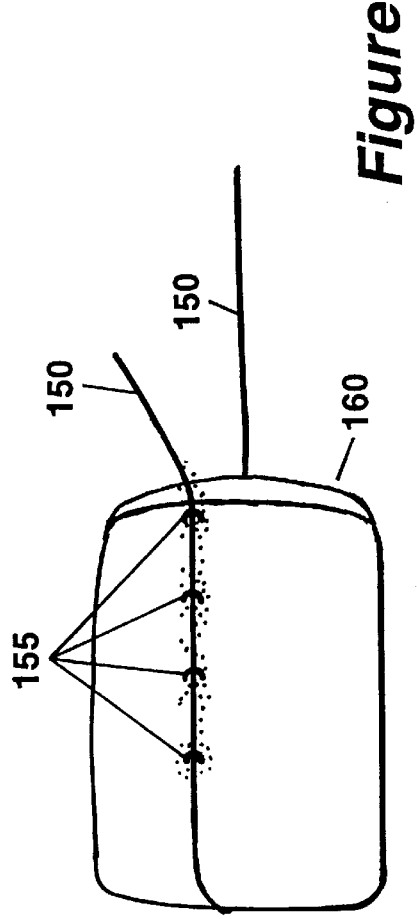
*Figure 11A*
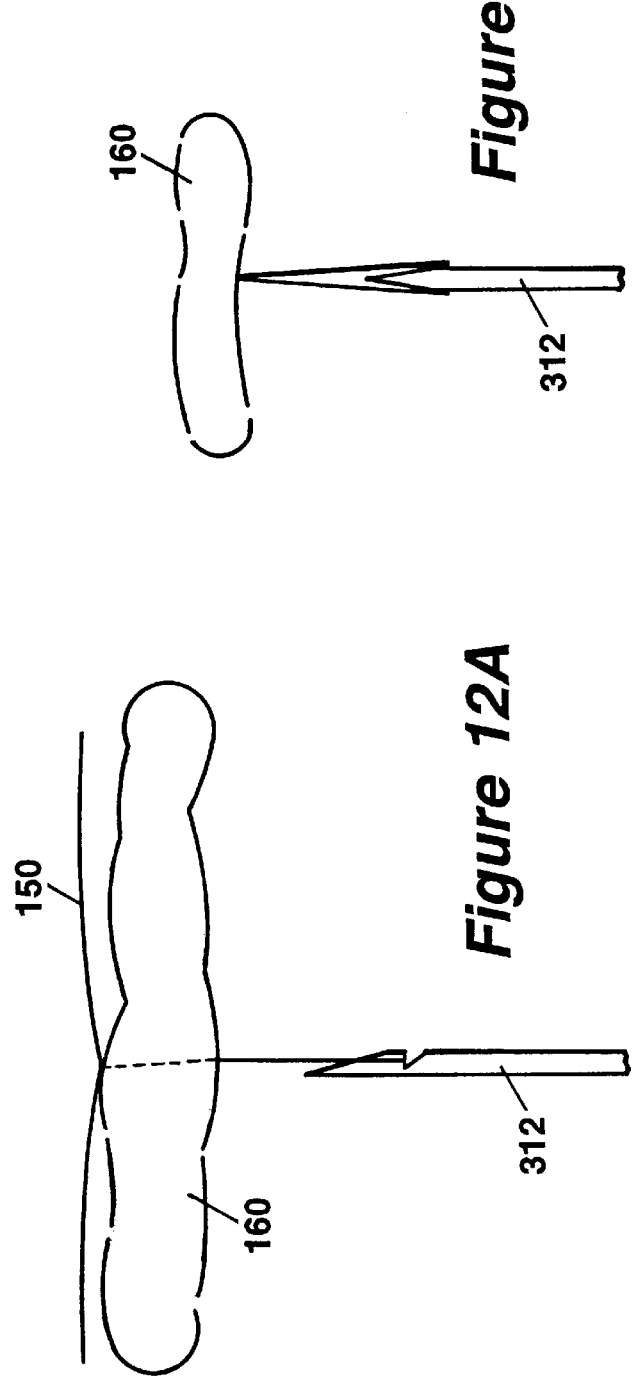
*Figure 12A*
*Figure 12B*

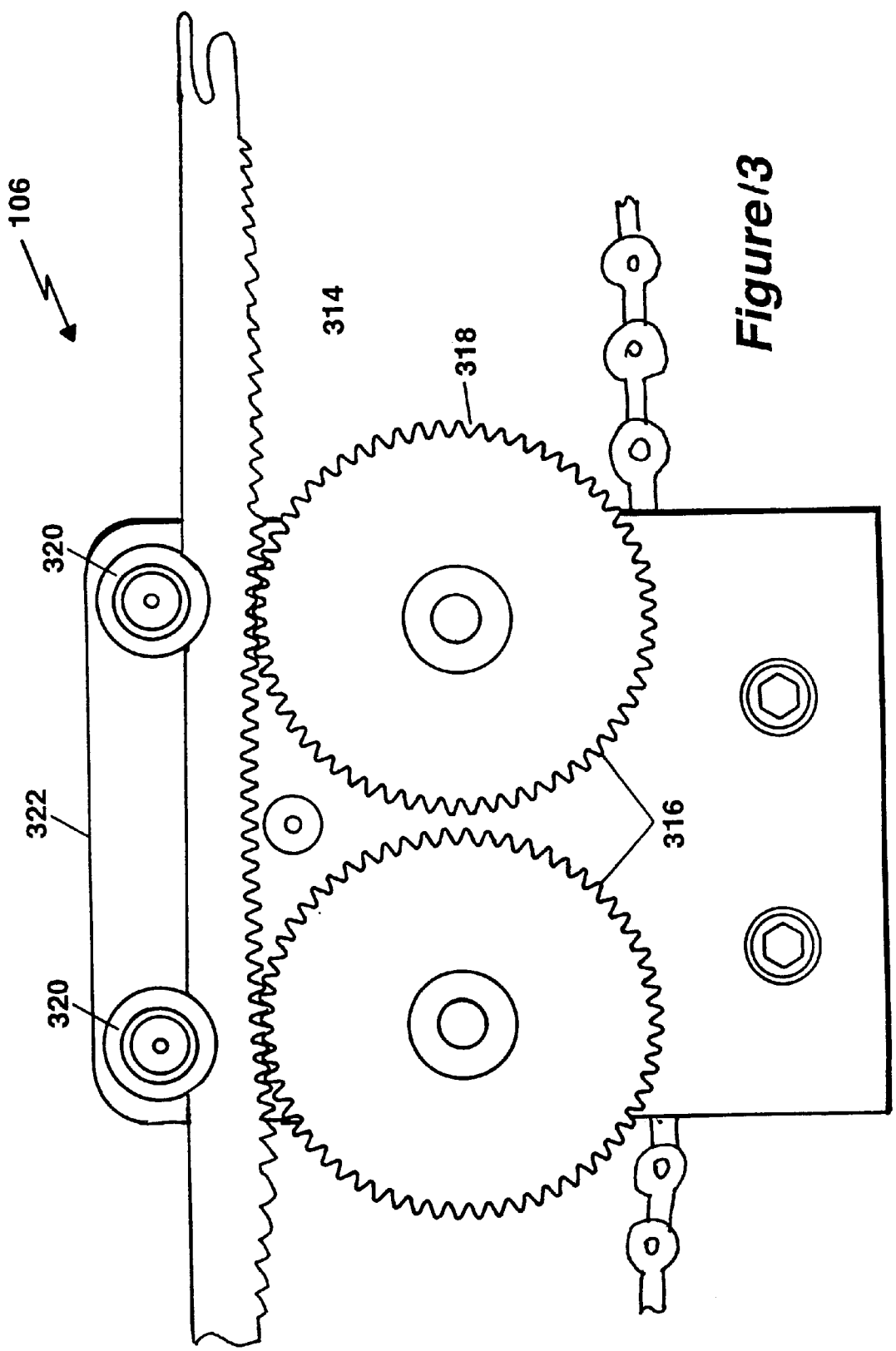

APPARATUS FOR HIGH-SPEED LACING OF AN ARTICLE

RELATED APPLICATION

This application is based on a provisional U.S. patent application entitled, ARTICLE OF MANUFACTURE AND APPARATUS FOR HIGH SPEED MANUFACTURE THEREOF filed May 1, 1998 by Daniel R. Shepard and assigned Ser. No. 60/083,968.

In addition, this application is the one of four U.S. patent applications filed on an even date herewith by Daniel R. Shepard, including:

Ser. No. 09/301,179, Attorney Docket No. G0005/7002, by, Daniel R. Shepard, entitled "METHOD AND APPARATUS FOR HIGH-SPEED LACING OF AN ARTICLE";

Ser. No. 09/301,174, Attorney Docket No. G0005/7003, by, Daniel R. Shepard, entitled "SHUTTLE APPARATUS FOR HIGH-SPEED LACING OF AN ARTICLE"; and Ser. No. 09/301,167, Attorney Docket No. G0005/7004, by Daniel R. Shepard, entitled "METHOD AND APPARATUS FOR HIGH-SPEED LACING OF A TEABAG".

The subject matters of the above-identified copending patent applications are incorporated herein by this reference.

FIELD OF THE INVENTION

The present invention relates to the fields of automated manufacturing, and, more particularly, to an apparatus for attaching a strand of material, cord or wire to one or more pieces of material at high-speed.

BACKGROUND OF THE INVENTION

The attachment of a strand of cord, thread, wire or other material to one or more pieces of material presents challenges to today's high speed manufacturing processes. As an example, consider the tampon industry. The rate at which the product is consumed requires that a high speed manufacturing process be employed. Current tampon designs employ a withdrawal string, usually a cotton cord, to allow the user to remove the product after use. The cord must be firmly attached to the tampon pad, and must not shear the product or leave material behind upon withdrawal.

One current method for attaching a cord to a pad involves sewing the cord to the pad, although this technique has a variety of disadvantages. The piercing of a cord by the thread actually weakens the cord, thereby requiring a thicker cord to meet any strength specifications. The use of thread to attach a cord to a pad introduces the possibility of thread breakage or jamming of the sewing apparatus. Current high speed industrial sewing machines operate at rates that are typically insufficient to feed a subsequent high speed production line. As a result, multiple sewing stations are required and their respective outputs must be merged to feed a single production line. Such multiple stations operating near their maximum rated speed, as well as the merging mechanism, increase possibility and frequency of mechanical failures, jams, etc. Further, the reciprocating motion of traditional sewing machine movement, combined with the very thin and flexible handling qualities of thread, further increase the likelihood of jams, or mechanical failure.

Another method of attaching a cord to a pad involves punching of a cord once through the pad, and entanglement of the cord about the pad, i.e. with a knot or other restraining mechanism. Punching a cord once through a pad suffers from a lack of redundancy of attachment. Should the cord fail to puncture the pad, the needle fail to feed the cord properly, or the pad mis-aligned, the cord will not be attached to the pad. Also, the force on the cord during the use of the product assembly is undesirably concentrated at the single point where the cord is attached to the pad.

Cord entanglement does not offer the mechanical strength or integrity offered by a cord that is firmly attached to the pad since the cord can slip off. Simply tying a string to a pad in such a fashion creates a product which is prone to failure.

Accordingly, a need exists for a cord attachment mechanism that is fast enough to support a subsequent high speed production line and which meets the reliability requirements of its users.

SUMMARY OF THE INVENTION

The present invention discloses an article of manufacture and a method and apparatus for manufacturing the same. Specifically, an apparatus and method for attaching a cord to a piece of receiving material at high speeds comprises one or more pins which engage the cord, pierce the receiving material and draw the cord through the receiving material from the first side to a second side thereof so that at least one open loop is formed in the cord on the second side of the receiving material. The apparatus further comprises a shuttle mechanism which moves relative to the pin and engages an end portion of the cord drawing the cord through the open loop so as to complete the lacing stitch of the cord through the receiving material. The pin(s) may be implemented as a push pin and a spreader pin pair, movably mounted relative to each other, each of which are adapted to grasp the cord and penetrate the receiving material. The loop on the second side of the receiving material is formed as the push pin and spreader pin move relative to each other.

In accordance with one aspect of the invention, an apparatus for forming one or more loops of cord and a receiving material comprises a frame, at least one pin movably mounted to the frame and adapted to penetrate a piece of receiving material and draw a flexible cord from a first side of the receiving material through to a second side of the receiving material. The pin is further adapted to form an open loop in the cord on the second side of the receiving material. In one embodiment, the pin comprises a push pin and a spreader pin pair each having a first end adapted to receive the cord and penetrate the receiving material. The open loop in the second side of the receiving material is formed when the spreader pin and push pin move relative to each other. In other embodiment, a plurality of pins, movably mounted to the frame penetrate the receiving material and form a plurality of loops on a second side of the receiving material.

In accordance with a second aspect of the invention, a threading apparatus for forming loops in a piece of receiving material comprises the threading pin to capture a cord, a push pin having a first end adapted to receive the cord captured by the threading pin, and a spreader pin opposably mated with the push pin. An open loop is formed in the receiving material when the spreader pin moves relative to the push pin. In various embodiments, the push pin and spreader pin are movably mounted to each other and spring biased to return to a closed position. In accordance with a third aspect of the invention, a method of forming one or more loops in a piece of receiving material comprising the steps of (a) penetrating the receiving material with a pin having a first end adapted to penetrate the receiving material and engage the cord; (b) drawing the cord through the receiving material from a first side to a second side thereof;

and (c) forming an open loop at the second side of the receiving material In one embodiment, the pin comprises a pushpin and spreader pin pair which have first ends adapted to receiving the cord and penetrate the receiving material. In accordance with another embodiment, the loop is formed on the second side of the receiving material when the spreader pin and pushpin are moved relative to each other. In another embodiment, a plurality of pins penetrate the receiving material so as to form a plurality of loops on the second side of the receiving material.

BRIEF DESCRIPTION OF THE DRAWINGS

The above and further advantages of the invention may be better understood by referring to the following description in conjunction with the accompanying drawings in which:

FIGS. 2A–C are top, side, and cross-sectional plan views of a pushpin assembly in accordance with the present invention with the pushpin-spreading pin airs in various positions;

FIG. 11A is a perspective view of the article of manufacture in accordance with the present invention;

FIG. 12 is a plan view of the pushpin retrieving a cord in an alternative embodiment of the present invention;

FIG. 13 illustrates a shuttle and drive assembly in accordance with an alternative embodiment of the present invention;

DETAILED DESCRIPTION OF THE PREFERRED EMBODIMENT

Figure 1:
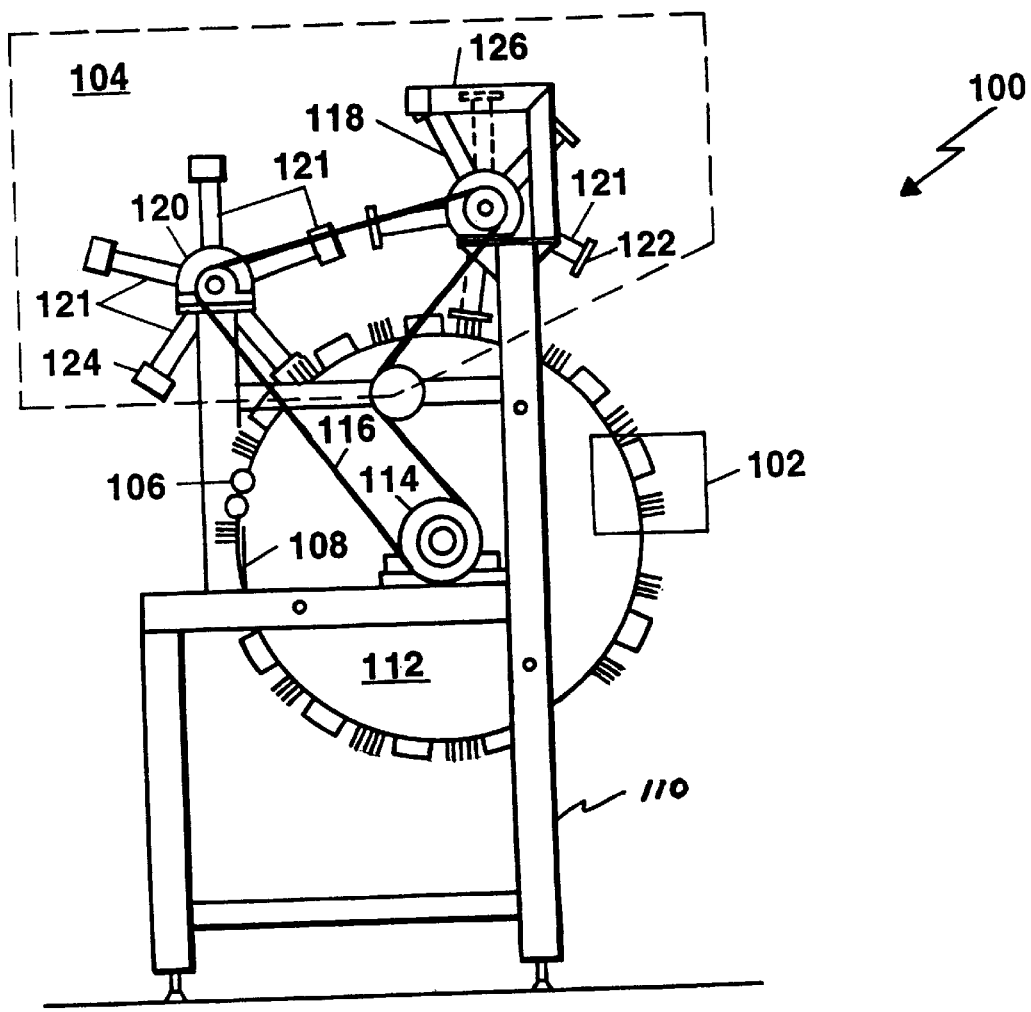
FIG. 1 is a diagram of the major elements of the apparatus in accordance with the present invention.

A high-speed lacing apparatus 100 in accordance with the present invention is illustrated diagrammatically in FIG. 1. In the illustrative embodiment, lacing apparatus 100 comprises a plurality of loop forming assemblies 102, receiving material feeding assembly 104, a plurality of loop threading assemblies 106, material removing assembly 108, and cord feeding assembly 109 (not shown in FIG. 1), and a rigid frame 110. Lacing apparatus 100 further comprises an assembly wheel 112, which rotates via a motor 114. In the illustrative embodiment, motor 114 is a direct drive motor which may be implemented with an electromagnetic motor or any other type of industrial-quality motor.

A plurality of loop forming assemblies 102 are mounted to assembly wheel 112. Each loop forming assembly 102 comprises a selected number of push pin assemblies 130 mounted between a pair of tandem gear wheels of a loop threading assembly 106. Loop forming assemblies 102 are described in greater detail with reference to FIGS. 2A–C. Loop threading assembly 106 is described in greater detail with references to FIGS. 3A–8 and 10A–B.

Receiving material feeding assembly 104 comprises a material feeding wheel 118, which is used to present a material to be laced upon the loop forming assembly 102, and a material positioning wheel 120. Both wheel 118 and wheel 120 may be driven by a belt drive 116 driven by drive motor 114. In an alternative embodiment, each wheel 118 and 120 may be driven by individual motors that operate in a synchronous rotation with assembly wheel 112. Both wheels 118 and 120 further comprise a plurality of spokes 121. As described in greater detail hereinafter, material feeding wheel 118 and holder 122 may be mounted in fluid communication so as to provide a source of negative pressure at the attachment surface of holder 122 so that pieces of receiving material may be collected and held by the negative pressure prior to presentation to the loop forming assemblies 102.

Figure 5:
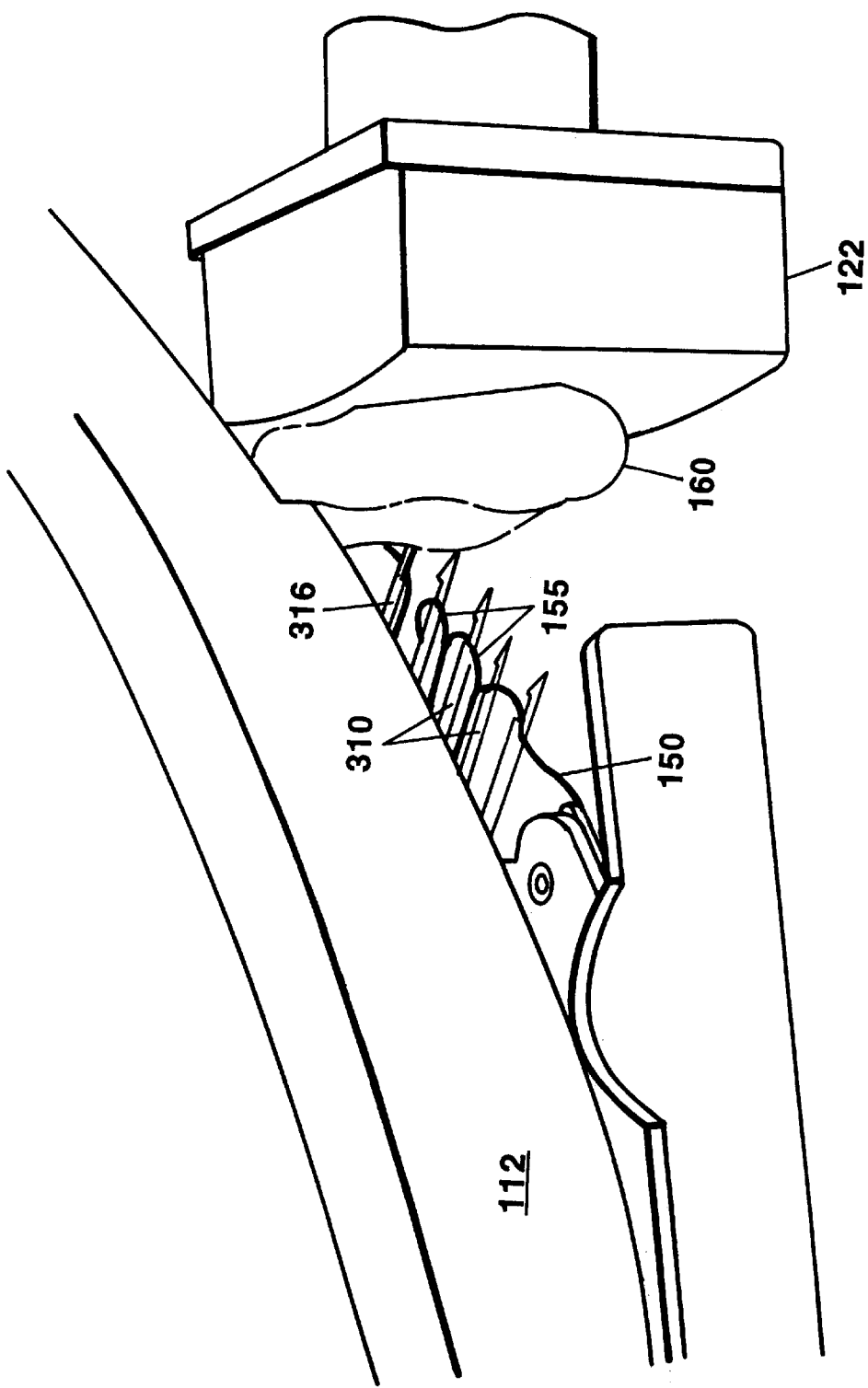
Figure 6:
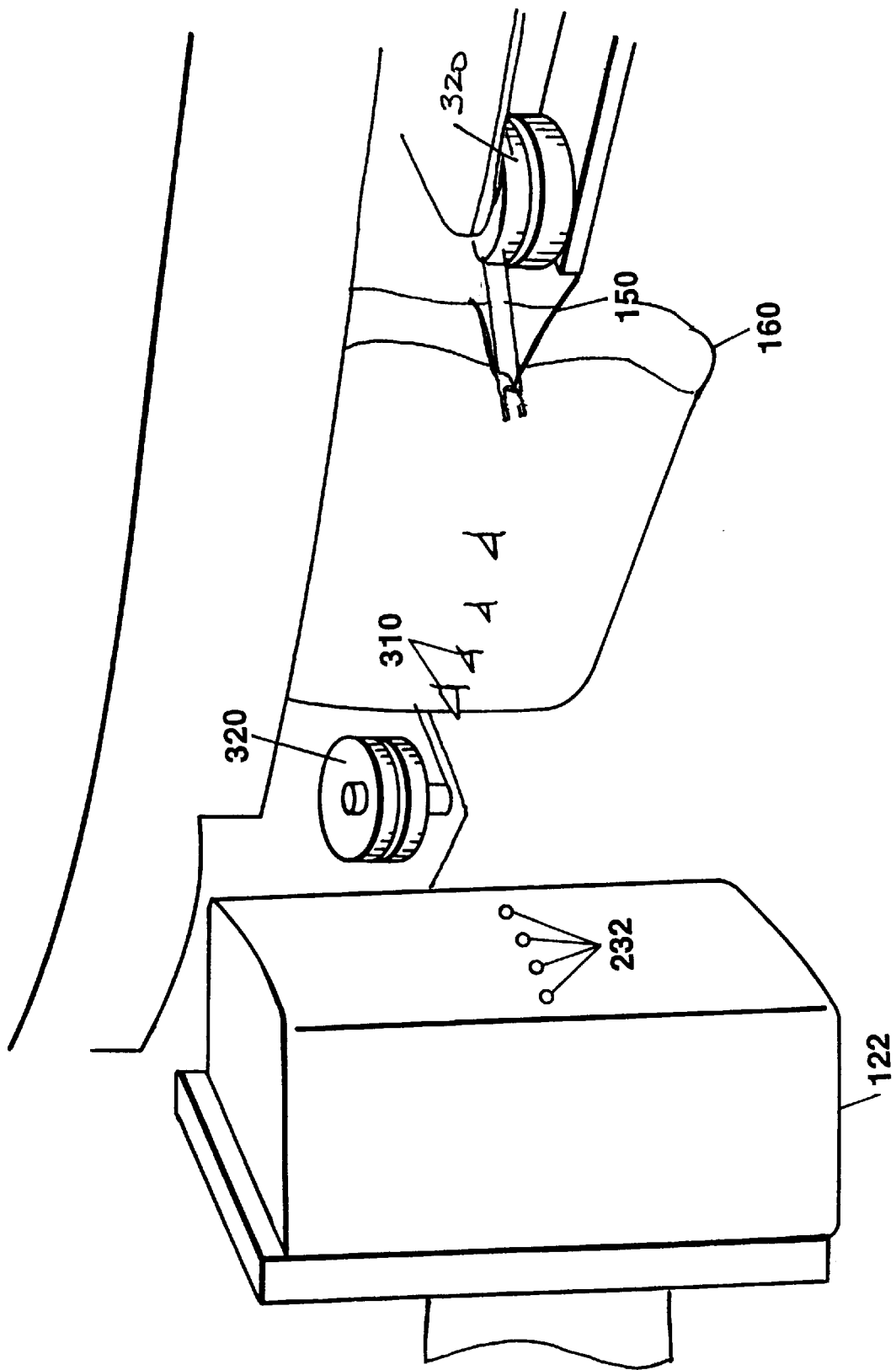

Mounted to the end of each spoke 121 of wheel 118 is a material holder 122, shown also in FIGS. 5–6. Material holder 122 securely grabs a piece of receiving material from one location and transports it to loop forming assembly 102. The purpose of material holder 122 is to secure the receiving material 160 for placement and then release it for alignment on the loop forming assembly 102. The material positioning wheel 120 includes a material compressing anvil 124 mounted to the end of each spoke 121 on the wheel. The anvil 124 is utilized to firmly position the receiving material 160 onto loop forming assembly 102 after being properly aligned by the material feeder wheel 118.

Once the receiving material is laced, the lacing cord is cut, and the laced material is removed by material removing assembly 108. Material removing assembly 108 may be two curved cutting elements that slip under the receiving material and pry it quickly off the loop forming assembly 102 as the assembly passes by removal assembly 108. In another embodiment, material removing assembly 108 may comprise a mechanical claw or clamp that firmly grasps the material and pulls it off loop forming assembly 102.

As illustrated, one or more of the assemblies comprising lacing apparatus 100 may be mounted movably or otherwise to a rigid frame 110. In the illustrative embodiment, rigid frame 110 is made of metal such as steel or aluminum. Similarly, assembly wheel 112, to which a plurality of push pin assemblies 130 and shuttle drive gear may be mounted, may likewise be made of aluminum or other rigid materials.

Pushpin/Threader Pin Assemblies

Figure 2A:
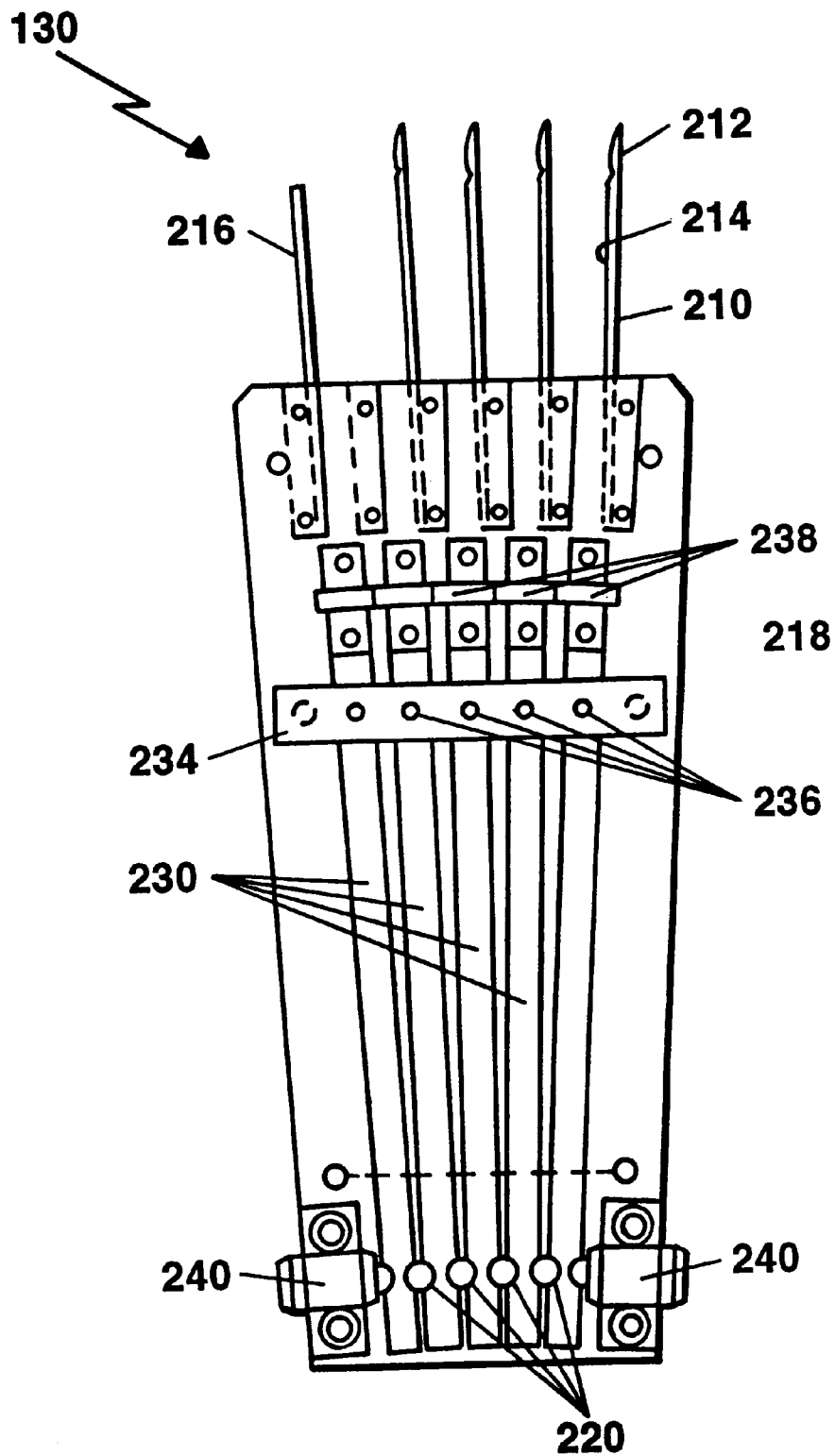

The loop forming assembly 102 comprises assembly wheel 112, shown in FIG. 1, having a plurality of push pin assembly stations 130 spaced about its circumference and mounted thereto. Referring to FIGS. 2A–C, each pushpin assembly 130 comprises a plurality of outwardly projecting pushpin pairs 210, a threaderpin pair 215, and a pin support 218. Each pushpin pair 210 further comprises a pushpin 212 mated to a second, closely-fitted spreader pin 214. Pushpin 212 includes a sharp, pointed tip 224 that tapers to form a J-hook notch 226. The pointed tip 224 is used to penetrate the receiving material. The J-hook notch 226 is used to hold the flexible cord during the loop-forming step of the present invention. Spreader pin 214 also includes a J-shaped hook 228, which has a lip sufficient to retain the flexible cord during the loop forming process as well.

Each pushpin assembly 130 also includes a threaderpin pair 215, which precedes the pushpins pairs 210 of an assemble 130. Each threader pin pair 215 comprises a threader pin 216 and threader spreader pin 217, each having a tapered end which serve to catch one end of the cord and align the cord to feed the shuttle. The threader pin 216 and threader spreader pin move in opposing directions relative to one another, thereby forming a loop in the cord in much the same fashion as pushpin pairs 210. In the illustrative embodiment, pushpin pair 210 and threading pin pair 215 may be made of stainless steel of other substantially rigid materials.

Referring to FIG. 2A, each pushpin pair 210 and threading pin pair 215 are held within a pin support 218. Pin support 218 may be implemented with a rigid metal base and further comprises support arms 230, spring plunger 232, support arm stop bar 234, stop adjustment screws 236, roller bearings 238, and spring mounted ball bearings 240, as illustrated. Support arms 230 pivotally clamp the pushpin and threading pin pairs so that the individual pins within each pair can separate at a prescribed time. A spring plunger 232 is mounted proximate to each spreaderpin support arm 230, which presses that support arm so that the pushpin or threader pin and its corresponding spreaderpin are aligned for piercing the receiving material. Support arm stop bar 234 comprises a stop adjustment screw 236 to set the alignment for each support arm and its pin pair. The pushpins and the threader pin are mounted to rigid support blocks which are part of pin support 218. In the illustrative embodiment, the pushpins are rigidly mounted since the push pin pairs are forcefully pressed through the receiving material. A roller bearing 238 is mounted on each support arm 230 which engages a stationary cam that is mounted proximate to rotating assembly wheel 112. The engagement of this cam pivots the support arm 230 and compresses the spring plunger 232 thereby causing the pin pair 210 to be spread. The support arms 230 are supported by ball bearings 220 in such a way that allows the support arms to be mounted on a slight arc that corresponds to the arc of assembly wheel 112 while at the same time enabling the support arms 230 to pivot in a direction perpendicular to that arc. Spring mounted ball bearings 240 hold the support arms 230 and the ball bearings 220 tightly together.

As described hereinafter in greater detail, pushpins 212 and spreader pins 214 are loaded with a flexible cord by the cord feeding assembly 110 and pushed through the receiving material causing the cord to double upon itself. The doubled up cord is then spread apart by the spreader pin 214, thereby forming a loop at each location of penetration, as explained thereinafter in greater detail.

Floating Shuttle and Drive Assemblies

Figure 3A:
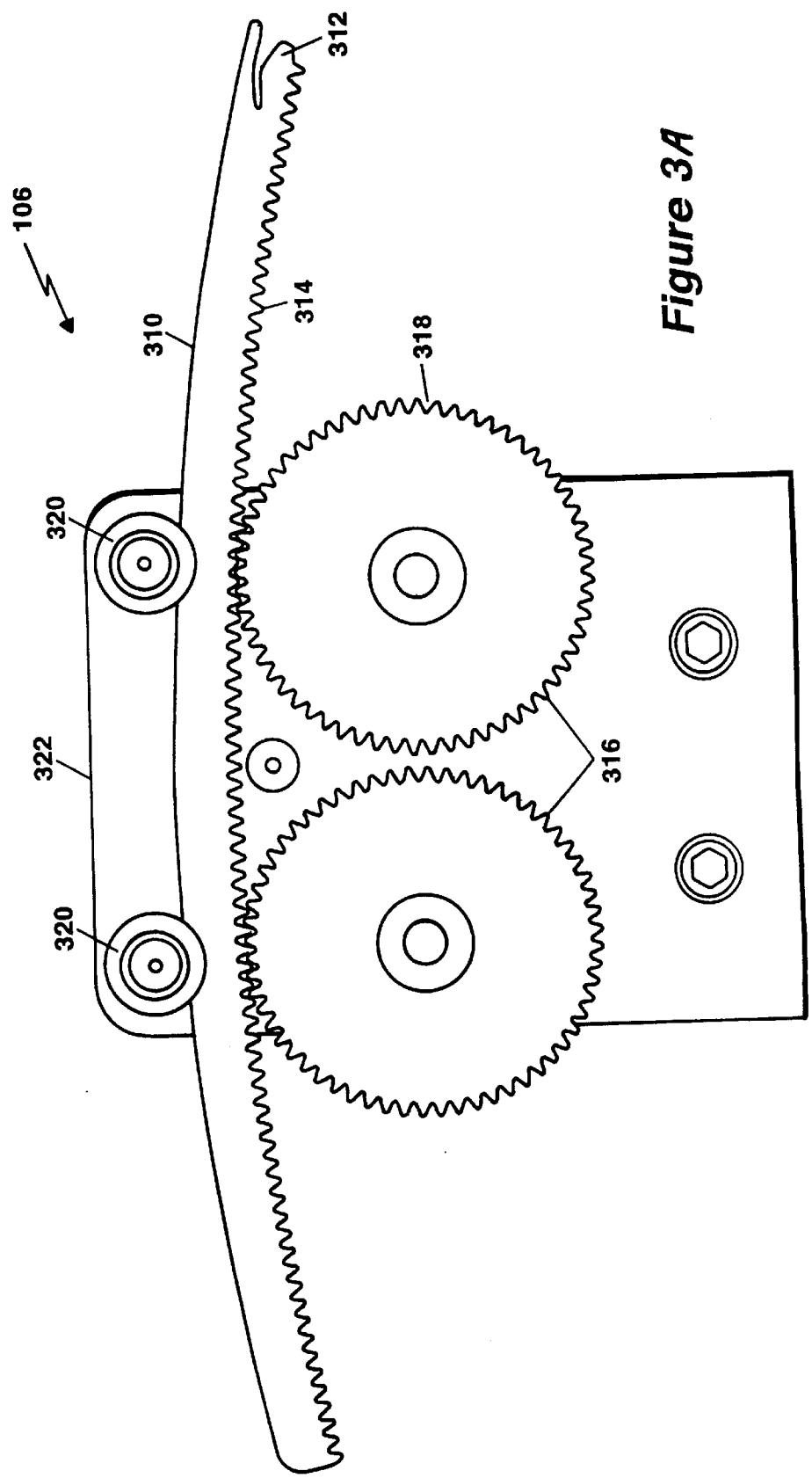
FIGS. 3A–B illustrate a shuttle and drive assembly in accordance with the present invention.
Figure 3B:
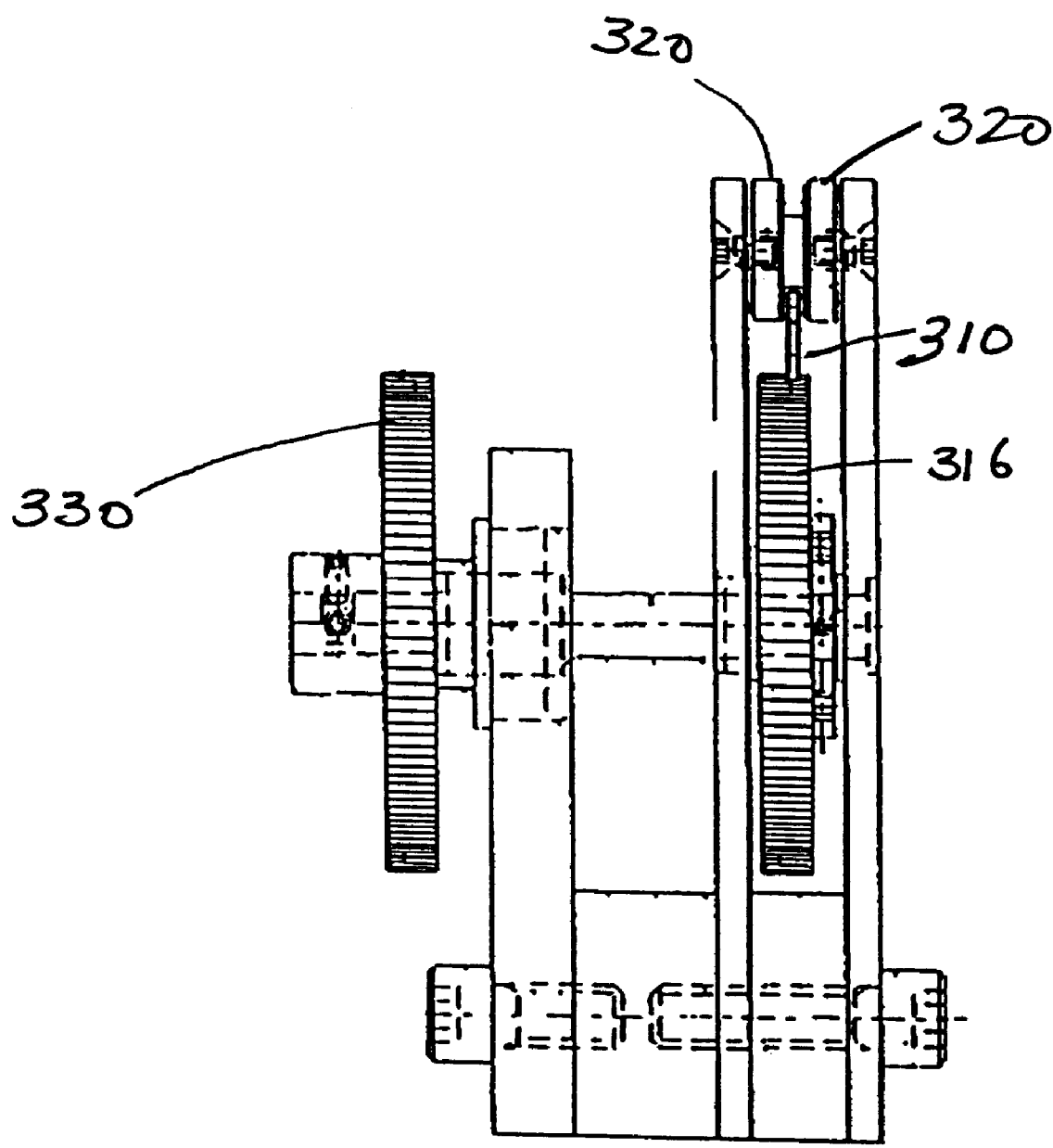

Loop threading assembly 106, as illustrated in FIGS. 3A–B, comprises a shuttle 310, support element 322, shuttle wheels 316 and retaining wheels 320. Shuttle 310 is designed to grasp a cord at one end and pass it through loops that are formed with the cord by the loop forming assembly 102. Shuttle 310 grasps the flexible cord via a thread hook 312. Thread hook 312 is a notched opening at the leading end of shuttle 310, as illustrated. Shuttle 310 has a generally flat, arcuate shape, and, in the illustrative embodiment, is made of metal or other rigid material. Along an inner radius of shuttle 310 a series of gear teeth 314 are provided. Gear teeth 314 mesh with a tandem pair of shuttle wheels 316. Shuttle wheels 316 turn in one direction that drives threading shuttle 310 along the outer radius of assembly wheel 112. Each wheel 316 includes a plurality of gear teeth 318 to match with the gear teeth 314 of shuttle 310. While engaged with tandem wheels 316, shuttle 310 is held in place by a pair of retaining wheels 320. Each retaining wheel is placed substantially opposite a matching wheel 316. Shuttle wheels 316 and retaining wheels 320 mount to a support element 322, which is also securely attached to assembly wheel 112. Support element 322 maybe substantially flat so as to allow wheels 316 and 320 to be movably mounted thereon.

In the illustrative embodiment, wheels 316 are driven by a stationary planetary gear (not shown) mounted to frame 110, with shuttle teeth 314 positioned parallel to the planetary gear so that pitch and the arc of the shuttle teeth 314 match the pitch and the arc of the teeth of the planetary gear. As shown in FIG. 3, one of a plurality of timing gears 330 that match the diameter and teeth of the shuttle wheels 316 is attached to each axle to which a shuttle wheel 316 is attached such that it will mesh with the teeth of this planetary gear. The planetary gear extends about the entire circumference of the assembly wheel 112 so that the timing gears 330 are never left floating freely. In this way, as assembly wheel 112 rotates, the timing gears 330 turn against the planetary gear thereby causing the shuttle wheels 316 to likewise turn. As a result, the surface speed at the point where the timing gears 330 mesh with the planetary gear and where the shuttle wheels 316 mesh with the shuttle 310 is exactly the same as the surface speed of the assembly wheel 112 along the same arc but in the opposite direction.

In an alternative embodiment, as illustrated in FIG. 13, the loop forming assemblies 102 could be mounted on a rotating flat endless loop, such as a chain and sprocket drive, in which case the shuttle 310 could be substantially straight and the path taken by the receiving material could be substantially straight, although other shaped paths and shuttles would be possible as well.

Cord Feeding Assembly

Figure 4:
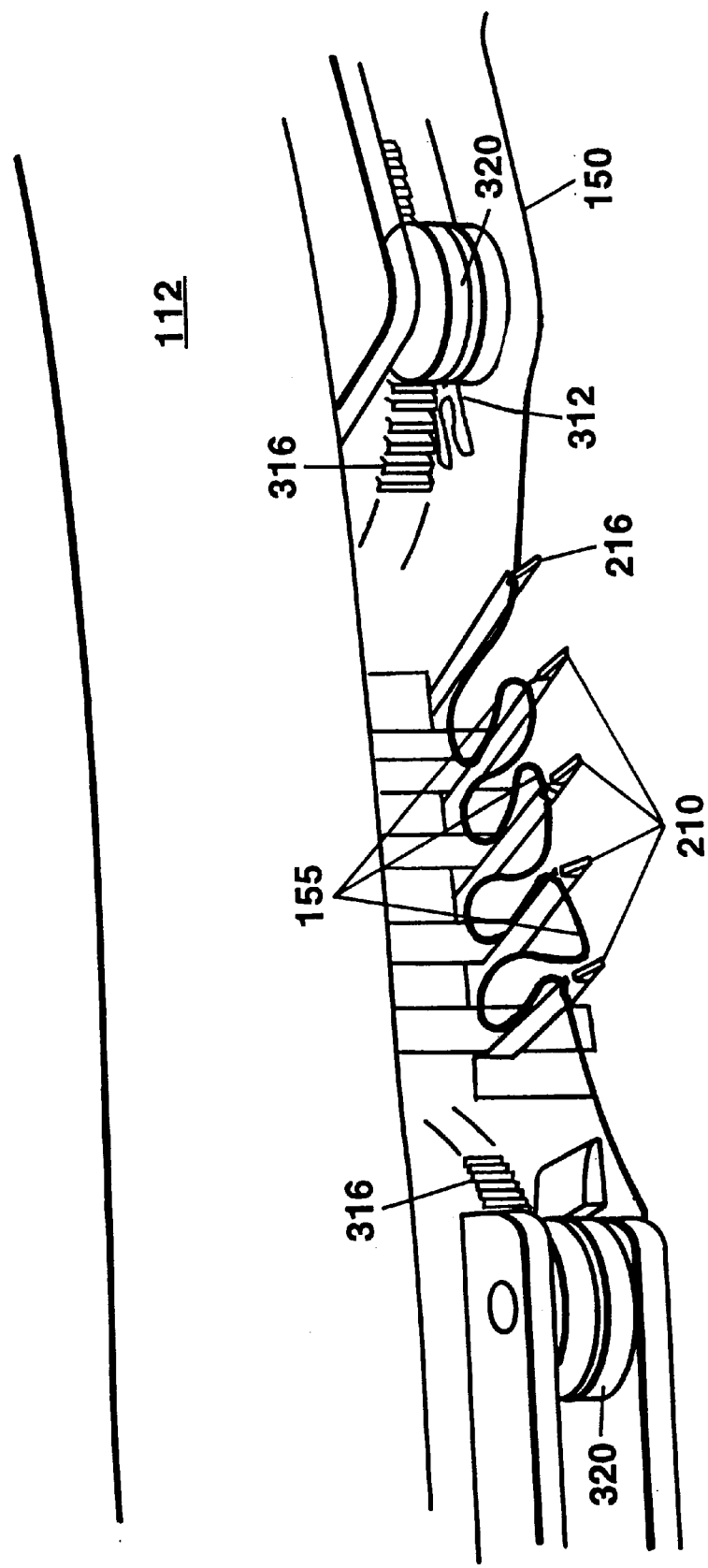
FIGS. 4–8 are perspective views of the pushpin assembly during the various steps in method of manufacturing an article in accordance with the present invention.

Referring to FIG. 4, a cord feeding assembly presents the cord 150 to the pushpin pairs 210 just prior to the receiving material 160 being pressed onto the pushpin pairs 210. When the receiving material is pressed to the bottoms of the pushpins, enough slack may be present in the cord at the point of each pushpin so that a partial loop can be formed. Because of the high speeds desired for the overall process, slack in the cord 150 cannot be achieved by allowing the cord to be pulled back through the pushpins 212 simply by pressing the receiving material 160 onto the pushpins 212 and then spreading the pushpins 212 and spreader pins 214 apart. Instead, slack is put into the cord 150 before the receiving material 160 is placed onto the pushpins 212. Furthermore, to prevent the resulting stresses on both the cord and the pushpins from creating this slack by pulling on the cord after it is already loaded in the push pins, the slack is put into the cord before it is inserted into the push pins. Accordingly, a mechanism is provided to restrain loops of slack which form between the respective push pin and spreader pin pairs within the pushpin assembly as described herein.

As used in the specification, the term "cord" is contemplated to embody not only cords but any strand, thread, filament, wire, cable, string, or fiber, etc., or other substantially small diameter flexible material capable of being manipulated and utilized in accordance with the apparatus, methods and article of manufacture described herein. Such cords and cord-like materials may be made from either synthetic or natural fibers as well as thin metal or resin filaments. The composition of the cords may be of a single fiber component or may be of a composite nature. The flexibility, tensile strength and diameter of the material depends on the nature of the receiving material and/or article with which the cord is to be utilized.

Figure 9:
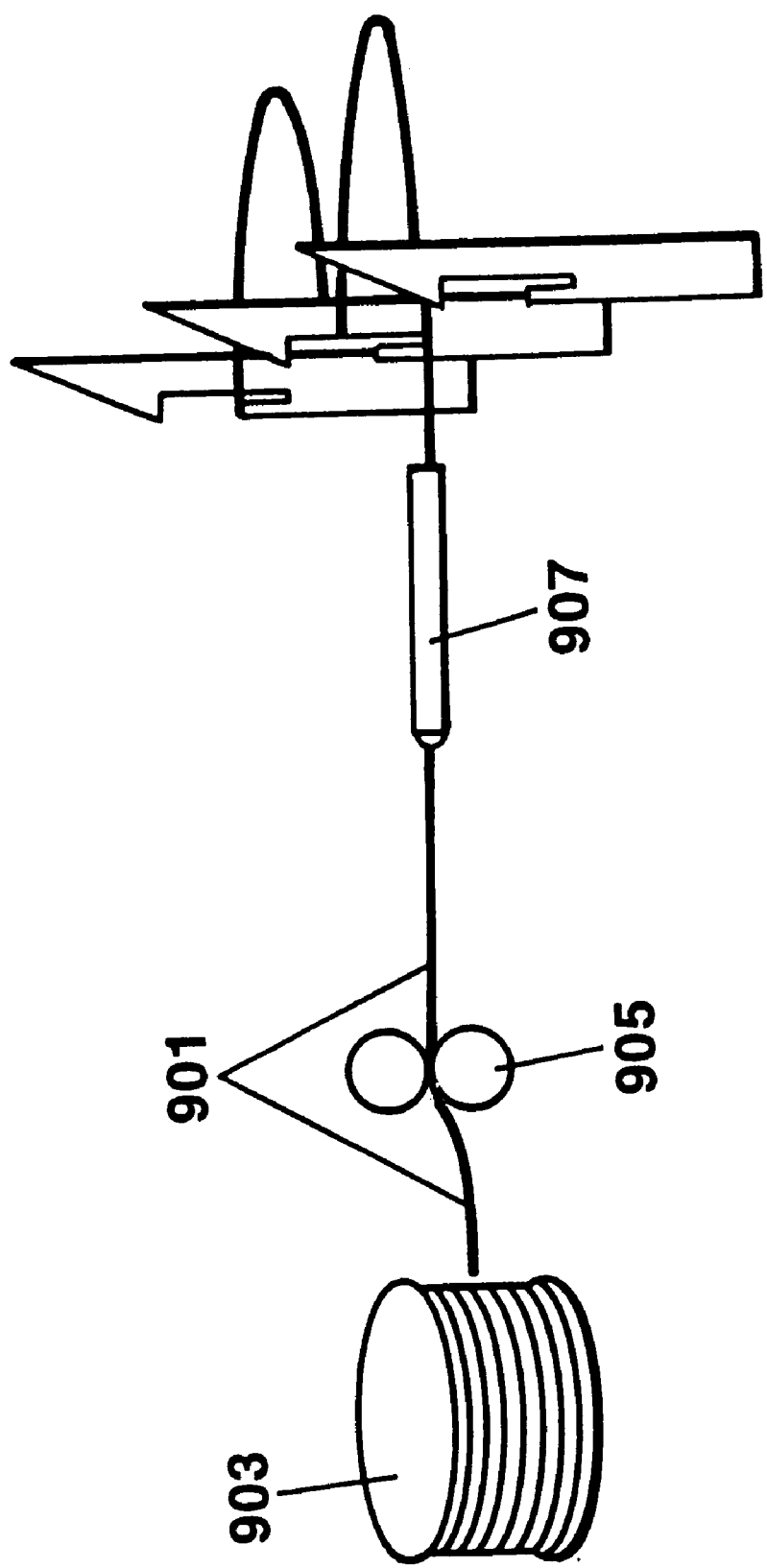
FIG. 9 is a conceptual diagram of a cord feeding assembly in accordance with the present invention.

A cord feeding assembly, in accordance with the present invention, is shown conceptually as feeding assembly 900 in FIG. 9. Feeding assembly 900 feeds cord 901 with slack into the pushpins 210. In the illustrative embodiment, feeding assembly 900 comprises a spool 903, feed pinch rollers 905, tube 907 and a source of positively pressurized air (not shown in FIG. 9). Feed pinch rollers 905 are rotated at a speed which draws cord 901 from spool 903 at a rate which maintains slack in the cord between spool 903 and feed pinch rollers 905. Cord 901 advances from pinch rollers 905 into tube 907. Tube 907 is coupled in fluid communication with a source of high pressurize air, which causes the cord to be jetted out from end of tube to the pushpin pairs 210. Since the pushpin pairs are in motion, cord is fed from one pushpin pair 210 to the next. The cord is fed to a pushpin assembly at a rate so that the portion of cord extending between any two adjacent pushpin pairs is longer than the spacing between any two adjacent pushpin pairs. As a result, the excess cord forms a partial loop of slack between the pushpin pairs, as illustrated in FIG. 9.

Lacing Method

To facilitate a better understanding of the apparatus of the present invention and the article of manufacture resulting therefrom, an outline of the process detailing the interaction of the receiving material and cord with the various components of the apparatus 100 is set forth below and with reference to FIGS. 4–11A.

FIGS. 4–11A illustrate various positions of the push pins 210 and assembly wheel 112 and their interaction with shuttle 310, material positioning wheel 120, and material compressing anvil 124, as well as the interaction of the various support gear assemblies and rollers. Specifically, FIG. 4 illustrates push pin assembly 130 mounted to assembly wheel 112 and surrounded by shuttle wheels 316 and 320. In FIG. 10, cord 150 is loaded onto the push pin/spreader pin pairs 210 using, for example the cord feeding assembly described with reference to FIG. 9. At this point in the manufacturing process, cord 150 has been loaded onto push pin pairs 210 and awaits receipt of receiving material 160.

In FIG. 5, illustrates the push pin assembly 130 and material positioning wheel 120 as they approach each other along there respective travel paths. Receiving material 160, in the form of a cotton pad, is positioned upon the surface of wheel 120 and is held in place, in the illustrative embodiment, by negative pressure supplied to the surface of wheel 120, for example, by a chuck in the wheel head or by other conventional means. As illustrated, push pin pairs 210 are about to commence piercing the receiving material 160.

FIG. 6 illustrates the receiving material 160 being partially impaled on the pushpin pair 210. As the pierced receiving material 160 separates from wheel 120, the heads of the push pins pairs 210 hold the receiving material in place. In the piercing step, receiving material 160 is pressed onto the tips of sharpened pushpins 212. A plurality of small apertures or holes 232 are formed in the surface of holder 122 so that the pushpins can penetrate completely through material 160 without breaking against holder 122. Apertures 232 are sized to account for the arc of the pushpins as they travel in proximity to material holder 122. The smaller apertures result in a greater surface area for providing counter-pressure during the actual piercing of material 160.

Figure 7:
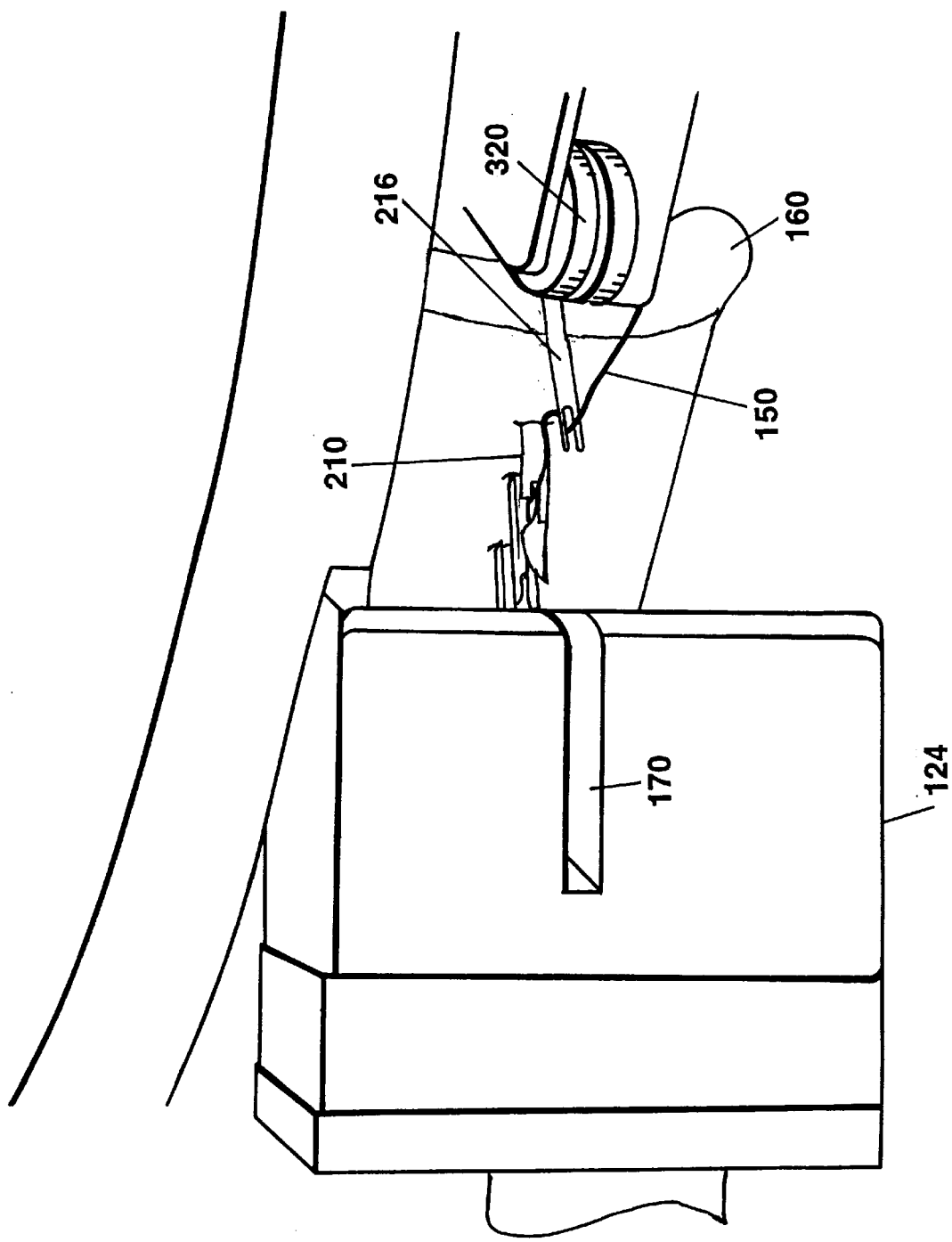

Next, as shown in FIG. 7, the material 160 is pressed just past the sharpened pushpins 212 by a synchronized compressing anvil 124. The compressing anvil 124 is synchronized to apply a counter-pressure upon material 160 to impale material 160 fully on the pushpin pairs 210. The exposed ends of pushpin pairs 210 pass through a deep slot 170 cut into the surface of the front of anvil 124.

In the illustrative embodiment of the invention, to minimize the stress on the pushpin pairs 210 when they are about to pierce material 160, it is preferred that the pushpins 212 contact material 160 at as close to a perpendicular angle as possible. This approach maximizes the piercing pressure of pushpins 212 while minimizing the lateral or bending pressure on the push pins 212. The deeper below the surface of anvil 124 that the push pins must travel the greater the arc along the anvil 124 that the pushpins and the counter-pressure anvil must overlap. In addition, the greater the arc means a greater angle is encountered when pushpin 212 meets the surface of anvil 124 at the point where pushpin 212 and the anvil 124 first begin to overlap. Therefore, pushpins 212 typically overlap with and cover a much greater arc of anvil 124 than the pushpins overlap with and cover an arc with material holder 122.

Figure 8:
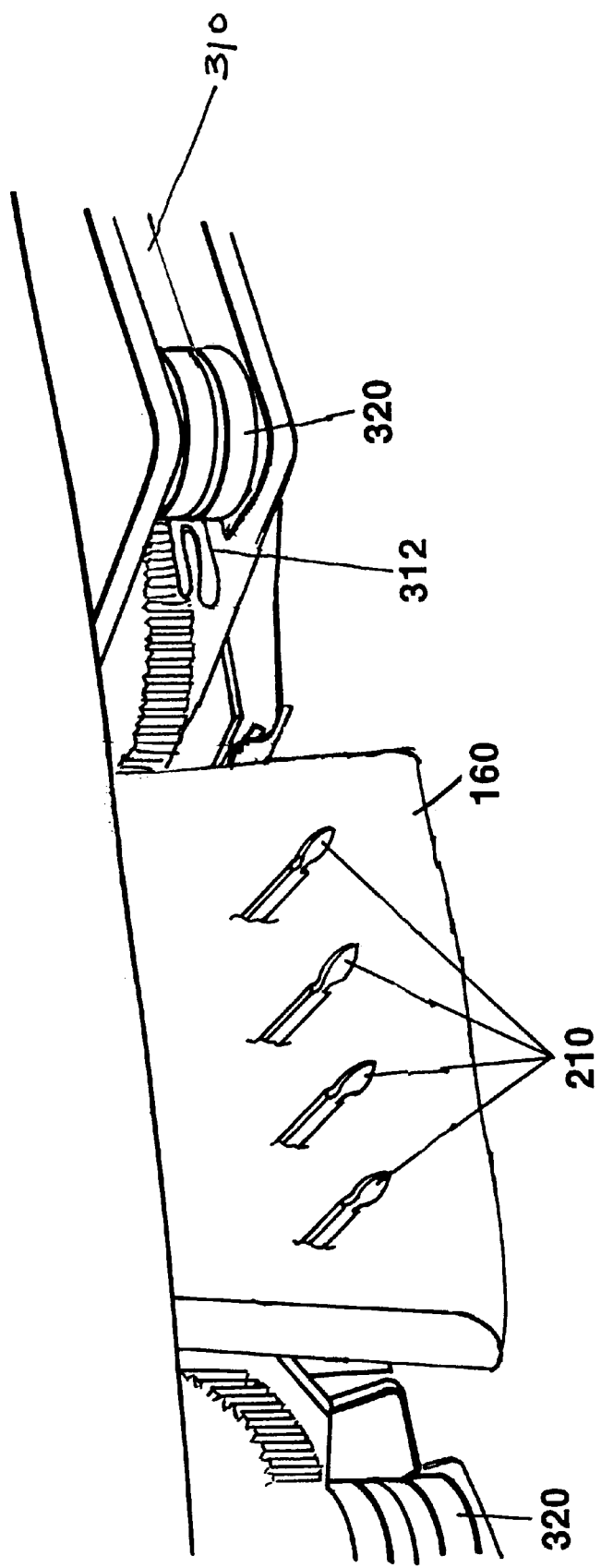

In FIG. 8, wheel 124 has pressed the receiving material 160 onto the push pin/spreader pin pairs 210 and the pad has disengaged from slot 170. At this point, cord 150 passes through threader pins 210, along a first side of receiving material 160 and thereafter alternating through the series of holes formed by push pin pairs 210 from the second side of receiving material 160 and back through to the first side of the receiving material. Next, assembly wheel 112 advances so that the roller bearings 238 engage a stationery cam, the front end of which is positioned just ahead of the loop threading assembly 106. The cam causes the spreading of the pushpin pin pairs 210, allowing shuttle 310 to pass through the loops in cord 150 formed on the opposite side of material 160. This stage is illustrated in FIGS. 10–11A.

Figure 10A:
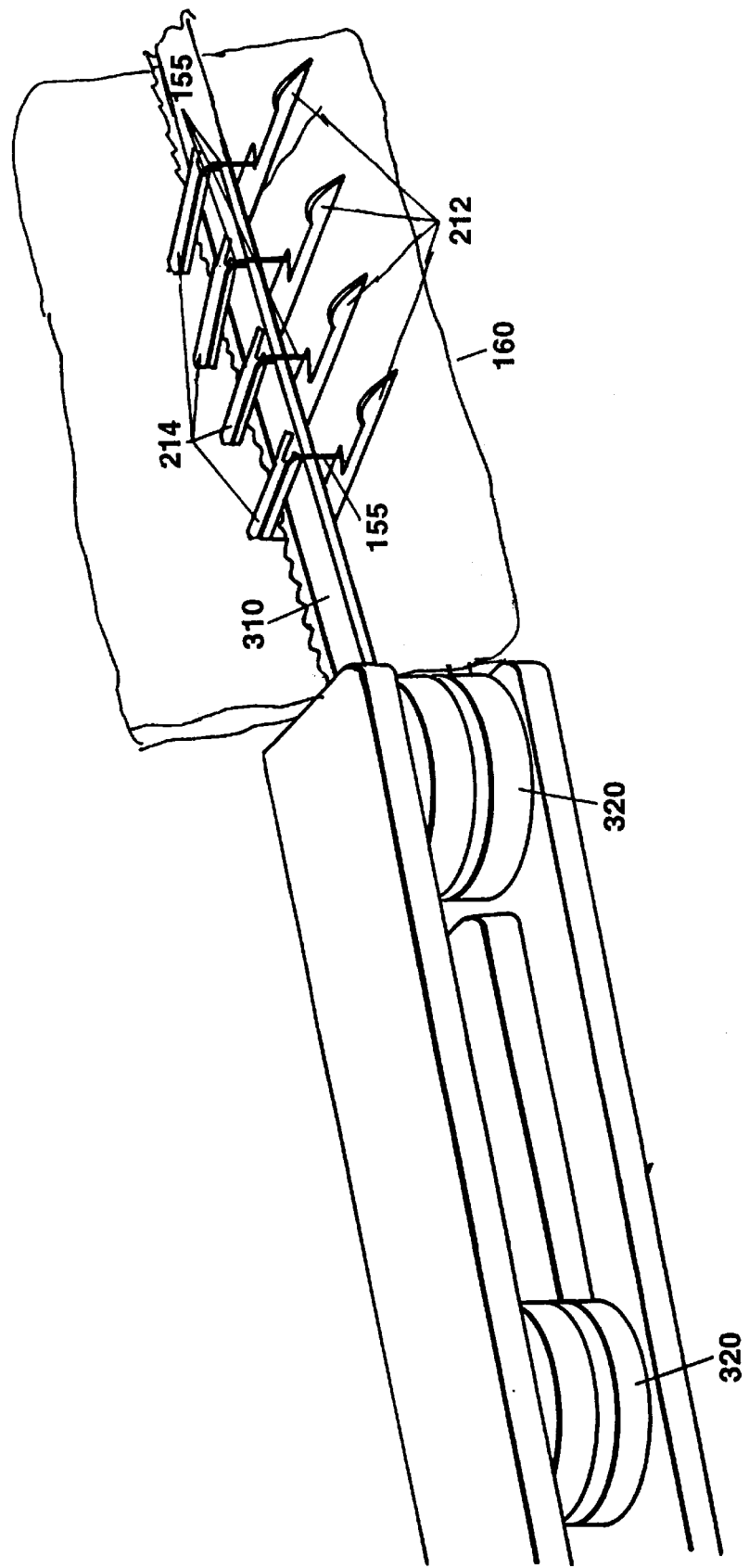
FIGS. 10A–B are perspective views of the pushpin and shuttle assemblies in accordance with the method of the present invention.

FIG. 10A depicts a more detailed illustration of how shuttle 310 traverses through loops 155 while pulling cord 150 through the loops 155. The rotation of assembly wheel 112 causes the receiving material 160 to move from left to right. As illustrated, each respective pair of pushpins 212 and spreader pin 214 are separated to form a plurality of open loops 155. Threading pin pair 216 is likewise spread to form a smaller loop 155 which is captured by the thread hook 312 of shuttle 310. Shuttle 310 passes through the centers of the larger pushpin loops 155 with cord 150 in tow.

In the illustrative embodiment of the present invention, shuttle 310 is not attached to the machine apparatus 100, but rather is supported by the series of supporting gears 316 and retaining wheels 320. This configuration enables shuttle 310, along with the end the cord 150, to pass into loops 155 at one end of the receiving material 160 and out of the loops 155 at the other end of receiving material 160 without the shuttle having to be retracted afterwards. This embodiment eliminates the prior art approach of using reciprocating needle and bobbin assemblies and their inherent disadvantages.

Gear wheels 316 are synchronized so that the surface speed of the gears as they mesh with shuttle 310 is the same, though of opposite direction, as the linear speed along an arc of material holder 122 at a radius that would reach the same point where the gears mesh with shuttle 310. Shuttle 310 is supported by wheels 316, which are movably mounted to the support 322. Consequently, shuttle 310 remains stationary as the forward rotation of assembly wheel 112 is offset by the backward rotation of tandem wheels 316. As shuttle 310 moves in a single direction relative to the rotation of assembly wheel 112, no reciprocating motion is required. The receiving material 160, held by the pushpins, approaches the front end of shuttle 310, the loops pass around the shuttle which captures the cord and draws it through the center of these loops. The receiving material with the now formed and threaded loops continues on past the tail end of the shuttle. Further, since the pushpin assemblies and the supporting gear assemblies are all mounted on assembly wheel 112, there is no possibility of the supporting gears ever colliding with and damaging any of the pushpins.

Figure 10B:
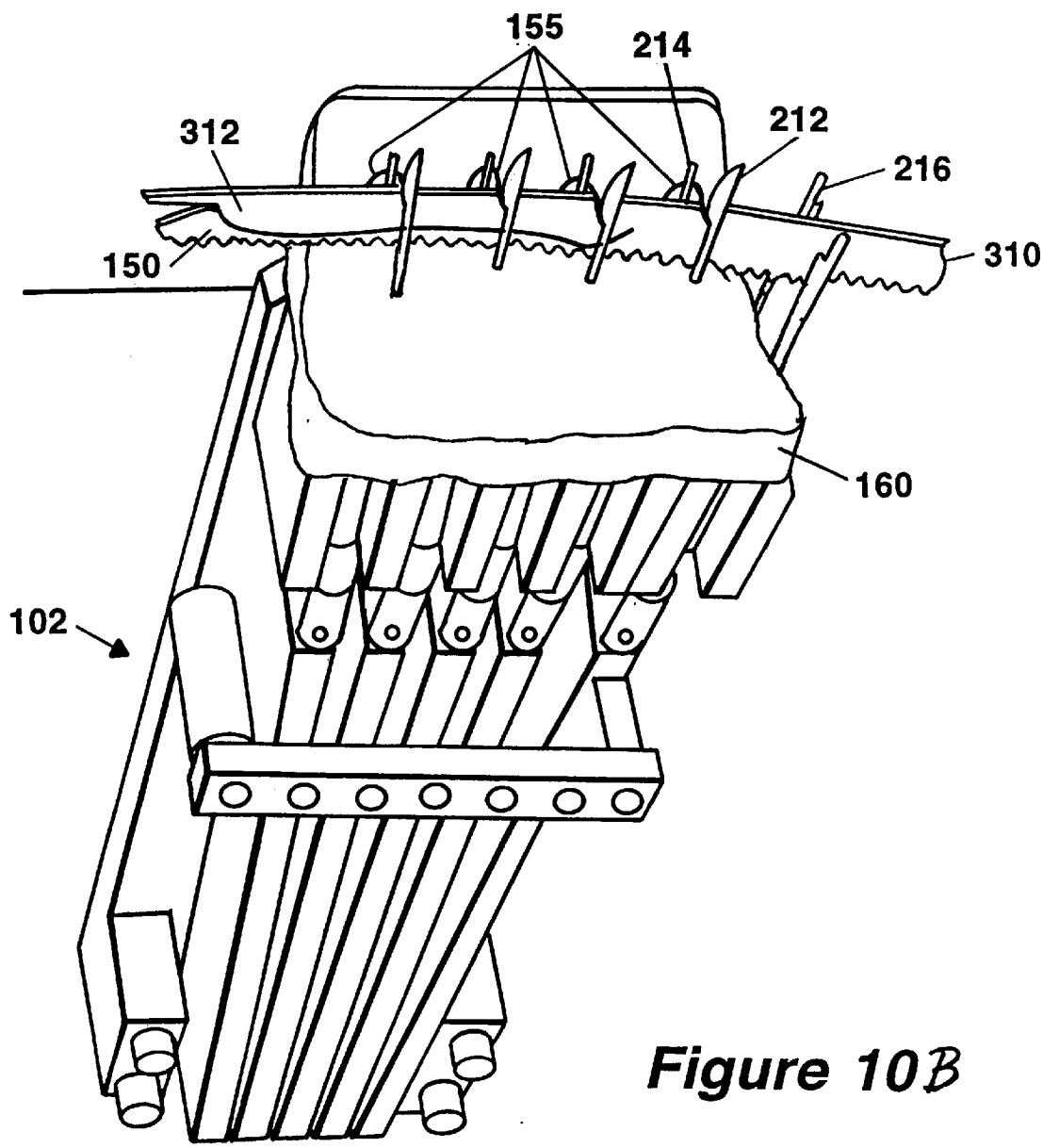

FIG. 10B illustrates, from a different perspective, the traversal of shuttle 310 through loops 155 formed by pushpin 212 and spreader 214. The pushpin assembly 130 utilizes an opening cam to separate the spreaderpins 214 from the pushpins 212. As the receiving material advances, supported by the pushpins, the pushpin assembly 130 engages the cam causing the opening of threading pin pair followed by the pushpin pairs in order. Once the threading pin pair is fully opened, the tip of shuttle 310 emerges from between the tandem wheels 316 and retaining wheels 320 of the preceding shuttle driver. In fact, since it is the shuttle 310 which is stationary and the pushpin assemblies 210, receiving material 160 and shuttle drivers are moving, the shuttle driver leading the piece of receiving material moves beyond the tip of the shuttle. As the shuttle advances relative to the pushpins it captures the cord at the spreader pins 214 where the top of the formed loop is lower. As the shuttle 310 continues to advance, it pulls the cord 150 through the centers of the now opened loops 155 formed by the pushpins. The tops of these loops are higher than the shuttle 310 thereby allowing the shuttle to pass through those loops. After passing through the loop formed by the last pushpin pair 210, the shuttle 310 is engaged by the tandem wheels 316 and retaining wheels 320 of the subsequent shuttle driver. At that point, the shuttle will cease to be supported by the leading retaining wheel pair of the preceding shuttle driver. The shuttle will instead be supported by the trailing retaining wheel pair of the preceding shuttle driver and the leading retaining wheel pair of the subsequent shuttle driver. The shuttle will be supported by both the preceding shuttle driver and subsequent shuttle driver until the shuttle is fully supported by both tandem wheel-retaining wheel pairs of the subsequent shuttle driver at which point the shuttle will cease to be supported by the preceding shuttle driver.

As the receiving material continues to advance beyond the tail end of the shuttle, the pushpin assembly 130 partially disengages the cam, e.g. the cam is stepped down causing the partial closing of the threading pin pair 216 followed by the pushpin pairs 210 in order until all are nearly closed. The pushpin pairs close until they are only the cord's thickness apart. This partial closing is sufficient to enable the removal of the laced material 160 from the pushpins. The pushpin pairs 210 do not close completely so that they do not scissor onto the cord, potentially cutting it. The pushpin pairs 210 remain in this nearly closed position until the pushpin assembly 130 has moved beyond the material removal assembly 108.

The removal assembly 108 removes the laced material 160 and cuts the cord 150. A series of parallel rails on either side of pushpins 212 and supporting gear assembly 316 rise under material 160 and lift the finished article off the pushpins. As the finished article is lifted from the pushpins, the cord, one end of which is still running back around the tip of the shuttle 310, pulls tight. This pulling causes loops 155 to lace tightly about the cord that had passed through the loops. After the loops are pulled to a desired tightness, but before the cord is stressed to the point of breaking, the removal path of the finished article causes the cord to be pulled across a blade or other cutting device (not shown) such that the cord is cut to a desired length. Other ways of pulling the cord tight and of cutting the cord will be apparent to one skilled in the art. For example, where cord 150 is implemented with a plastic or resin filament rather than a textile fiber, a mechanism for or severing the filament may, in addition to a cutting blade, be implemented with a heating element for melting the filament.

Laced Article

FIG. 10B illustrates a laced pad which comprises the article of manufacture of the present invention in which the cord 150 has been pushed through a first side of the receiving material 160 to form a plurality of sequential loops on the opposite side of the receiving material. Thereafter the loose end of cord 150 has been threaded from the first side of the receiving material to the second side of the receiving material and through the interior of each of the loops formed on the opposite side of the receiving material. In FIG. 10B, the laced pad does not yet have the cord pulled tight. FIG. 11A illustrates a finished article 175 of the laced receiving material 160 where loops 155 are laced tightly by cord 150.

Figure 11B:
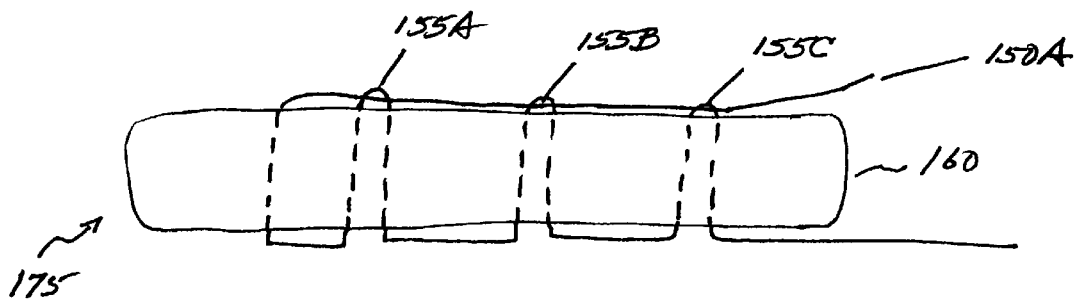
FIG. 11B–D are side views of the article of manufacture in accordance with the present invention.
Figure 11C:
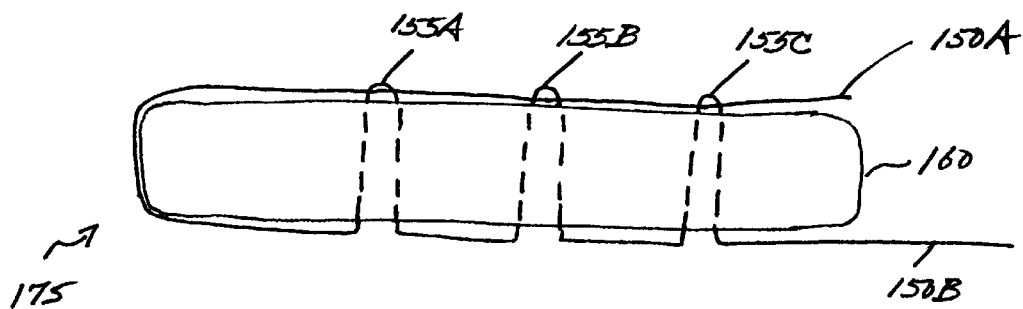
Figure 11D:
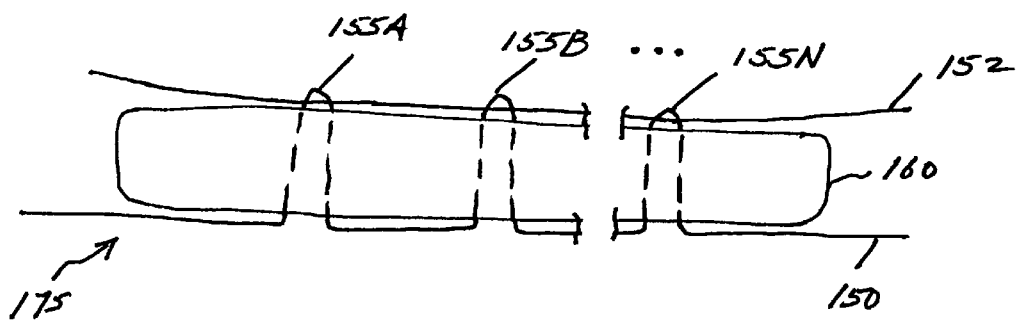

FIGS. 11B–11D illustrate an article of manufacture 175 made with the process and apparatus described herein. Specifically, FIG. 11B illustrates a side view of an article of manufacture 175 comprising a piece of receiving material 160 having a cord 150 laced through the receiving material, as illustrated. Specifically, the cord 150 passes through the receiving material from a first side thereof at a plurality of locations to a second side thereof to form loops 155A–C on a second side thereof. In FIGS. 11B–C the cord path through the interior of receiving material 160 is illustrated in phantom. In FIG. 11B, an end portion 150A of cord 150 reenters receiving material 160 and emerges on the second side thereof and then passes through open loops 155A–C as illustrated. In the illustrative embodiment, the other end of cord 150, end portion 150B may have a trailing length, as illustrated. As shown in FIGS. 11b–C, substantially all of the slack removed from loops 155A–C so that the stitch formed by cord 150 is tightly secured to receiving material 160.

FIG. 11C illustrates an alternative embodiment of the article 175 of FIG. 11B. In this embodiment, the end portion 150A rather than repenetrating receiving material 160 prior to passing through loops 155A–C, instead extends around the exterior surface of an end of receiving material 160 and then into loops 155A–C. With this embodiment, the end portion 150A does not penetrate the receiving material 160, therefore eliminates the need for an extra pin to penetrate the receiving material.

FIG. 11D illustrates an alternative embodiment of the article 175 of FIG. 11B–C. In this embodiment, a completely separate cord 152 passes through loops 155A–C, instead of the end 150A of cord 150. This embodiment is useful where a large number of loops 155A–N penetrate the receiving material 160. In this embodiment, instead of shuttle 310 grasping the end 150A of cord 150, as previously described herein, a separate second cord 152 is disposed within the path of shuttle 310 as the article is advanced toward the shuttle. The shuttle then grasps the second cord and draws the cord 152 through the open loops 155A–N in a manner similar to that described previously. The second cord may be supplied to the shuttle using a system similar to that described with reference to FIG. 9.

Figure 15B:
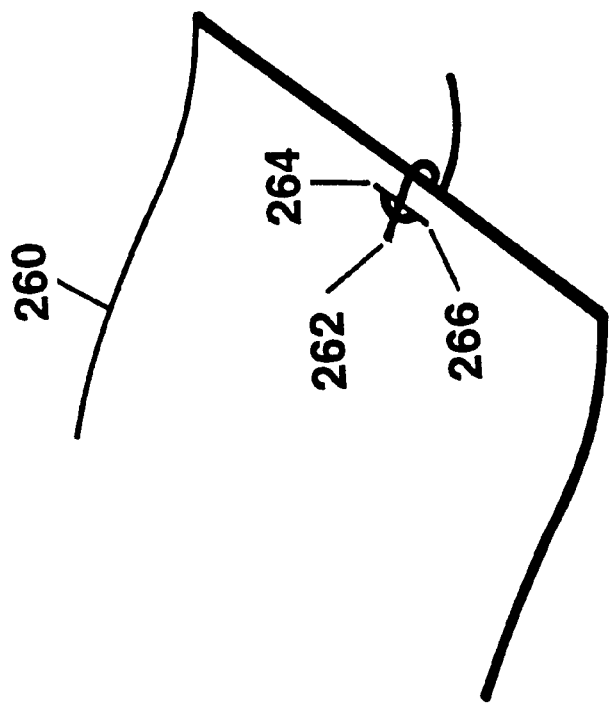
FIGS. 15A–B illustrate the process steps used to attach a cord to a tea bag in accordance with the methods of the present invention.
Figure 15A:
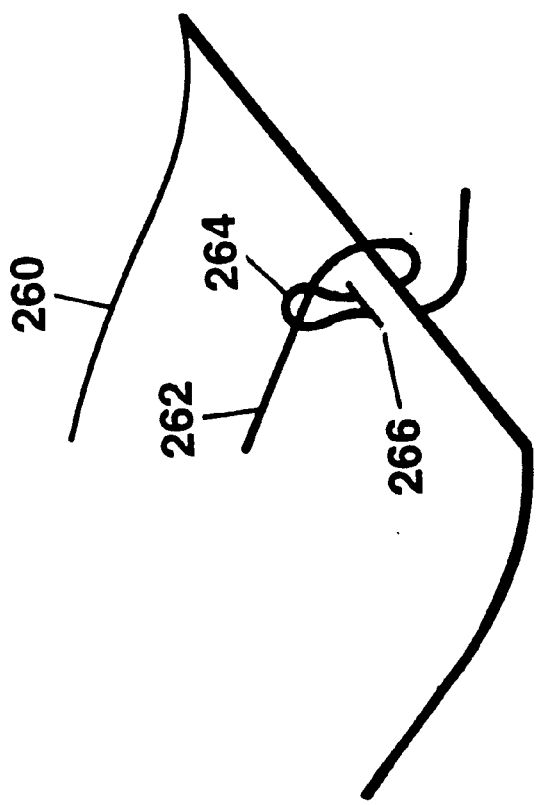

As stated previously, the concepts and implementation described herein may be applied to any situation where a strand of material, such as a cord, thread, wire, or fiber is to be attached to a piece of receiving material. For example, apparatus 100, may be utilized to attach a string to a tea bag. In this embodiment, the cord-like substance is a string of the thickness and strength typically used with conventional tea bags. The receiving material is the tea bag itself. Since the weave of the paper used to form the bag is rather loose, the subject invention is ideally suited to lace the string onto the bag without overstressing or tearing the bag in the process. Using the push pin assemblies and shuttle, as described previously, with appropriate changes in the dimensions made to accompany the size of the receiving material, i.e., the tea bag, a cord 262 may be laced to a tea bag 260, as illustrated FIGS. 15A–B. Specifically, FIG. 15A illustrates a portion of a tea bag 260 in which a cord 262 passes from one side of the tea bag 260 through a slot 266 to a second side of the tea bag where an open loop 264 is formed. An end portion of the cord 262 is then drawn through the open loop 264 using the loop threading assemblies and methods described herein. The cord 262 is then tightened to remove any slack from the loop 264 and cut in a manner previously described. In the resulting tea bag 260, as illustrated in FIG. 15B, the thread 262 is securely fastened to the bag in a manner which does not employ staples or glue as in conventional tea bag structures.

In an alternative embodiment, the tea bag 260 may be scored during its manufacturing process and before it is supplied to apparatus 100 to form the slot 266 prior to being penetrated by the pushpins of the pushpin assembly. Such scoring of the bag may be achieved by means of a perforating wheel that passes over the outer edge of the tea bag 260 prior to the bag being presented to the pushpins. Alternatively, a cutting die may stamp the outer edge of the bag to form a slit. Other conventional methods and systems for forming the slot 266 may be used as well.

Figure 14A:
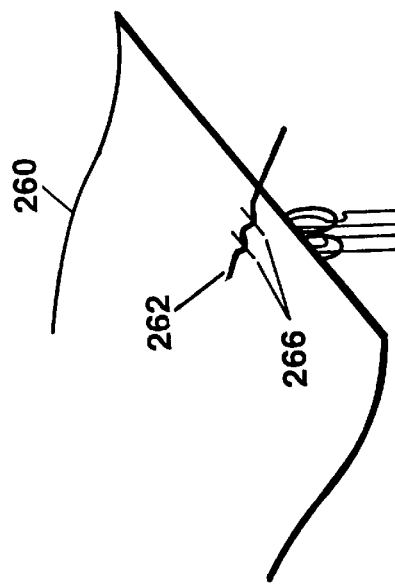
FIGS. 14A–D illustrate the process steps used to attach a cord to a tea bag in accordance with the methods of the present invention.
Figure 14B:
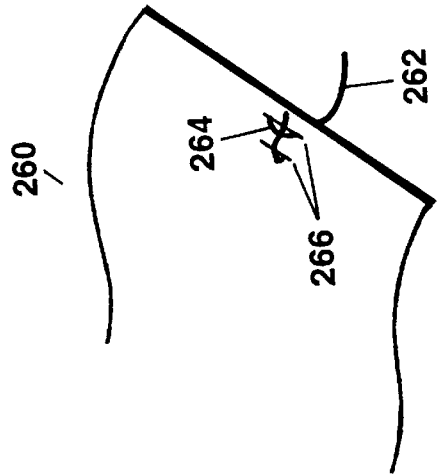
Figure 14C:
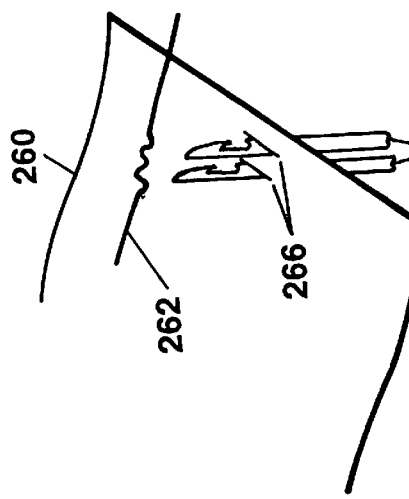
Figure 14D:
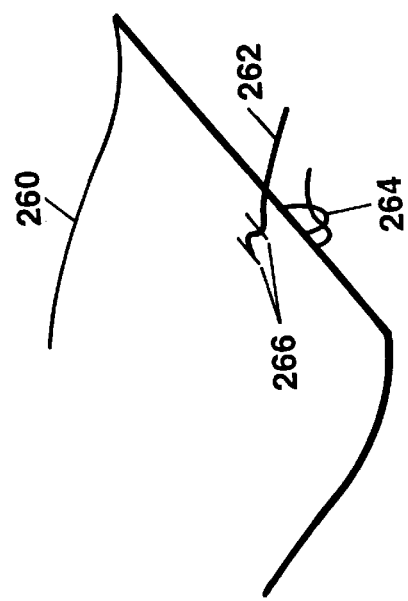

FIGS. 14A–D illustrate various stages in the method of attaching a cord 262 to a tea bag 260 in accordance with the present invention. In a manner similar to that previously described with reference to FIGS. 12A–B, a pair of pushpins 312 are not loaded with cord 262 but draw the cord from one side of the tea bag 260 to another after having penetrated the bag. Specifically, as illustrated in FIG. 14A, pushpins 312 penetrate tea bag 260 at lots 266. Slots 266 may be precut as described previously or may be made by push pins 312. Cord 262 is disposed on a first side of the bag 260 as illustrated. Pushpins 312 are designed similar to pins 210 and are shaped so as to engage cord 262 and draw the cord from a first side of tea bag 260 through slots 266 to a second side so as to form a pair of open loops at the second side thereof, as illustrated in FIG. 14B. A shuttle similar to those previously described herein, may be used to grasp the cord 262 and draw the cord through open loop 264 as illustrated in FIG. 14C. The shuttle continues through loop 264 drawing cord 262 to eliminate any slack in the loop. An end portion of cord 262 proximate to the portion grasped by the shuttle and drawn through loop 264 in FIG. 14C is cut either before or after threading through loop 264 using any of the techniques previously described. FIG. 14-D illustrates the resulting laced tea bag 260 which shows the underside of the bag, not visible in FIGS. 14A–C, illustrating the end portion of cord 262 extending through loop 264.

As stated previously, various modifications to the dimensions, shapes and sizes of the various assemblies of apparatus 100 may be necessary to adapt the technology to use with a tea bag, such modifications within the scope of those reasonably skilled in the art in light of the disclosure contained herein. For example, pushpins 312 do not need to be accompanied by spreader pins, since the open loops formed on the second side of the tea bag have a relatively small diameter. The tea bag illustrated in FIGS. 15A–B is manufactured similar to that described with reference to FIGS. 14A–D, except that a single slot 266 is present.

With the illustrative embodiment, sewing apparatus 100 can sustain rates in excess of 500 attachments per minute, and may produce a cord attached to the pad by a lacing stitch that may have pull strengths in excess of 5 kilograms. Of course, the high-speed lacing apparatus can be used for applications and products other than the personal hygiene product example described herein, for example, any production process in which a cord, thread, wire, or fiber is attached by lacing to a receiving piece of material. Also, the receiving material 160 may comprise any natural, synthetic or composite material capable of being pierced and threaded. For example, the apparatus and methods described herein may be applied to the process of attaching a string to a tea bag, as described in one of the previously referenced copending applications.

Alternative Embodiments

Several variations are possible to the article, method and apparatus disclosed herein. First, if the cord to be attached was made of an elastic-like material, the slacking mechanism may not be necessary as the open loops could be created by stretching the cord and a loop tightening mechanism may not be necessary as the loops would snap back into place as the push pins are removed.

Second, the floating shuttle mechanism can be used in any environment where an item is to be passed through a full (O-shaped) or partial (C-shaped) aperture. In addition, although in the illustrative embodiment shuttle 310 is shown having an arcuate shape, and pushpin pairs 210 move in a circular motion relative thereto, other implementations are possible. For example, the pushpin assemblies may move linearly in to a straight shuttle or they may move in an ovoid or other shape relative to the shuttle. Any path in which a loop forming mechanism moves relative to a stationary shuttle may benefit from the concepts disclosed herein.

Third, the pushpins 212 can pierce through the receiving material to be laced, be loaded with the cord on the other side and then pull back through the receiving material such that the loops are then formed on the same side of the receiving material as the push pins. This example is illustrated in FIGS. 12A–B.

Fourth, if the loops are formed by pulling the push pins back through the material, the width of the loop could be formed by the width of the push pin, as illustrated in FIG. 12A (side view) and FIG. 12B (top view showing the loop opening) with the shuttle being fed through a narrower loop.

Fifth, the needle and spreader pair could be replaced with a single needle and a cam such that once the cord was passed through the receiving material to be laced, the cam would capture the cord and spread the cord out into a loop.

Sixth, the supporting gears could be replaced by supporting devices other than gears such as a chain and sprocket drives or friction belts. Retaining wheels keep the shuttle aligned during operation.

Seventh, the supporting gears could be turned at a speed other than the forward speed of the receiving material thereby making the relative difference in the speed of the shuttle to that of the receiving material other than that of the speed of the receiving material through the machine. This may, however, require that additional shuttle handling mechanisms be provided to return one or more shuttles to their starting points.

Eighth, two rotating surfaces can be formed where the material to be laced is held against the outer rotating surface. An inner surface containing the push pins would have a smaller diameter and would rotate about an axis that is off center to the axis of the outer surface such that the push pins would extend through the outer surface at one area of the rotation.

Ninth, the shuttle could be sized so that it could be driven and supported by a single drive gear.

Tenth, the shuttle supporting mechanisms could be modified such that the shuttle could be supported by a single support mechanism, for example, a single retaining wheel.

Eleventh, although receiving material feeding assembly 104 and cord feeding assembly 109 are part of lacing apparatus 100 in the illustrative embodiment, such assemblies may be implemented as separate apparatus which interact with lacing apparatus 100 provided appropriate drive mechanism are used to coordinate and synchronize the timing of the interaction of the respective assemblies described herein.

Although various exemplary embodiments of the invention have been disclosed, it will be apparent to those skilled in the art that various changes and modifications can be made which will achieve some of the advantages of the invention without departing from the spirit and scope of the invention. These and other modifications are intended to be covered by the appended claim.

What is claimed is:

1. An apparatus for forming one or more loops of cord in a piece of receiving material comprising:
    a frame; and
    at least one push pin and spreader pin pair movably mounted to the frame and adapted to receive the cord and to penetrate the piece of receiving material and draw a flexible cord from a first side of the receiving material through to a second side of the receiving material;
    the push pin and spreader pin being further adapted to form an open loop in the cord on the second side of the receiving material when one of the spreader pin and push pin move relative to the other.

2. The apparatus of claim 1 further comprising a plurality of push pin and spreader pin pairs movably mounted to the frame and adapted to penetrate the piece of receiving material and draw the flexible cord from the first side of the receiving material through the second side of the receiving material, the push pin and spreader pin pairs being further adapted to form open loops in the cord on the second side of the receiving material.

3. The apparatus of claim 1 wherein the push pin and spreader pin pair are adapted to penetrate the receiving material, engage the cord on the first side of the receiving material, draw the cord back through the receiving material to the second side of the receiving material, and form an open loop at the second side of the receiving material.

4. The apparatus of claim 1 wherein the push pin and spreader pin pair are adapted to engage the cord at the first side of the receiving material, penetrate the receiving material thereby drawing the cord from the first side of the receiving material through to the second side of the receiving material, and form an open loop at the second side of the receiving material.

5. A threading apparatus for forming loops in a piece of receiving material, the threading apparatus comprising:
    a pushpin having a first end and a second end, the first end adapted to capture a cord;
    a spreader pin, opposably mated to the push pin, a first end of the spreader pin adapted to receive the cord, the first end of the spreader pin placed proximate the first end of the pushpin, the open loop formed on the second side of the receiving material when the spreader pin moves relative to the push pin; and
    a threading pin adapted to engage the cord.

6. The apparatus of claim 5 wherein the pushpin and spreader pin each have a notch at the first end thereof for engaging the cord.

7. The apparatus of claim 5 wherein a plurality of pushpin pairs, each having one pushpin and one spreader pin, are mounted adjacent one another.

8. The apparatus of claim 7 wherein the pushpin and spreader pin pairs are spring biased to return to a predetermined position.

9. The apparatus of claim 8 wherein the predetermined position can be individually adjusted for each pushpin and spreader pin pair.

10. The apparatus of claim 7 wherein each pushpin pair is pivotally coupled to another pushpin pair.

11. The apparatus if claim 5 wherein the second end of the pushpin is pivotally coupled to one of a second end of a spreader pin, or a second end of a second pushpin.

12. The apparatus of claim 5 wherein the threader pin is adapted to engage the cord prior to a portion of the cord being threaded through the open loop.

13. A method of forming one or more loops in a piece of receiving material comprising:
    (a) penetrating the receiving material with a pin having a first end adapted to penetrate the receiving material and to engage the cord, the pin comprising a push pin having a first end adapted to receive the cord and to penetrate the receiving material, and a spreader pin movably mounted to the push pin, the spreader pin having a first end adapted to penetrate the receiving material;
    (b) drawing the cord through the receiving material from a first side of the receiving material through to a second side of a receiving material; and
    (c) forming an open loop at the second side of the receiving material with the pin by moving one of the spreader pin and push pin relative to the other.

14. The method of claim 13 wherein the step (c) comprises the step of:
    (c.1) moving one of the spreader pin and push pin in a direction away from the other.

15. The method of claim 13 wherein step (a) comprises the step of:
    (a.1) penetrating the receiving material with a plurality of pins having a first ends adapted to penetrate the receiving material and to engage the cord.

16. The method of claim 15 wherein the plurality of pins each comprise a push pin having a first end adapted to receive the cord and to penetrate the receiving material, and a spreader pin movably mounted to the push pin, the spreader pin having a first end adapted to receive the cord and to penetrate the receiving material.

17. The method of claim 16 wherein the step (c) comprises the step of:
    (c.1) moving one of the spreader pins and push pins relative to the other.

18. The method of claim 16 wherein the step (c) comprises the step of:
    (c.1) moving one of the spreader pins and push pins in a direction away from the other.

19. A method of forming one or more loops in a piece of receiving material comprising:
    (a) penetrating the receiving material with a pin having a first end adapted to penetrate the receiving material and to engage the cord;
    (b) drawing the cord through the receiving material from a first side of the receiving material through to a second side of a receiving material;
    (c) forming an open loop at the second side of the receiving material with the pin; and
    (d) maintaining the open loop until a portion of the cord is passed through the loop.

* * * * *